(12) United States Patent
Leban et al.

(10) Patent No.: US 7,423,057 B2
(45) Date of Patent: Sep. 9, 2008

(54) COMPOUNDS AS ANTI-INFLAMMATORY, IMMUNOMODULATORY AND ANTI-PROLIFERATORY AGENTS

(75) Inventors: Johan Leban, Munich (DE); Bernd Kramer, Aachen (DE); Wael Saeb, Planegg-Martinsried (DE); Gabriel Garcia, Munich (DE)

(73) Assignee: 4SC AG, Martinsried (DE)

( * ) Notice: Subject to any disclaimer, the term of this patent is extended or adjusted under 35 U.S.C. 154(b) by 0 days.

(21) Appl. No.: 11/355,903

(22) Filed: Feb. 17, 2006

(65) Prior Publication Data
US 2006/0199856 A1 Sep. 7, 2006

Related U.S. Application Data

(60) Division of application No. 10/193,526, filed on Jul. 9, 2002, now Pat. No. 7,176,241, which is a continuation of application No. PCT/EP01/07948, filed on Jul. 10, 2001.

(51) Int. Cl.
| | |
|---|---|
| A61K 31/40 | (2006.01) |
| A61K 31/164 | (2006.01) |
| A61K 31/341 | (2006.01) |
| A61K 31/381 | (2006.01) |
| C07D 207/24 | (2006.01) |
| C07D 333/06 | (2006.01) |
| C07D 307/30 | (2006.01) |

(52) U.S. Cl. .................. 514/423; 514/448; 514/471; 514/615; 514/423; 548/530; 549/64; 549/476; 562/504

(58) Field of Classification Search .......... 514/615, 514/423, 448, 471; 562/504; 549/64, 479; 548/530
See application file for complete search history.

(56) References Cited

U.S. PATENT DOCUMENTS 4,661,630 A  4/1987  Harigaya et al.

FOREIGN PATENT DOCUMENTS

| DE | 25224929 | 12/1976 |
|---|---|---|
| DE | 2 851 379 | 5/1979 |
| DE | 2 921 002 | 11/1979 |
| DE | 3 346 814 | 6/1984 |
| EP | 0 097 056 | 12/1983 |
| EP | 217206 | 4/1987 |
| EP | 0 646 578 | 4/1995 |
| EP | 780128 | 6/1997 |
| JP | 50-121428 | 9/1975 |
| JP | 50121428 * | 9/1975 |
| JP | 55-157547 | 12/1980 |
| WO | WO 97/34600 | 9/1997 |
| WO | WO 99/38846 | 8/1999 |
| WO | WO 99/45926 | 9/1999 |

OTHER PUBLICATIONS

Chan et al., "New N- and O-Arylations with PHenylboronic Acids and Cupric Acetate", Tetrahedron Letters, 39, 1998, pp. 2933-2936.

Leadbeater et al., Tetrahedron, No. 55, 1999, pp. 11889-11894.

Bew et al., "Experiments on the Synthesis of Azasteroids", J. Chem. Soc., 1995, pp. 1775-1777.

McDonald et al., "The Synthesis of Several Dimethyl $\Delta^1$ Cycloalkene-1,2-dicarboxylates and Certain 4-Substituted Bicyclo[201.0]pentane-1-carboxylic Acids", J. Org. Chem., vol. 37, No. 15, 1972, pp. 2418-2422.

Owsley et al., "A Variable Temperature Preparative Scale Photochemical Reactor. Cis-Dimethyl Bicyclo[3.2.0]Heptane-1,5-Dicarboxylate", Org. Prep. Proc. Int., vol. 3, No. 2, 1971, pp. 61-70.

Lee et al., "Preparation and {4+2} Cycloaddition Reactions of 3-Sulfolene-3,4-dicarboxylic Acid and its Derivatives", Bull. Inst. Chem. Academia Sinica, No. 40, 1993, pp. 1-10.

Baker et al., "the Structure of 2-Alkyldihydrothiophene-3,4-Dicarboylic Acids", J. Org. Chem. 13, 1948, pp. 123-133.

Baker et al., "Penthiane-3,4-Dicarboxylic Acid", J. Org. Chem. 12, 1947, pp. 328-332.

Paquette et al., "Probing of the Interrelationship Between Heteroatomic Substitution and Equillbrium Imbalance in 2,8-Trimethylenesemibullvalene Derivatives", J. Am. Chem. Soc., vol. 97, No. 21, 1975, pp. 6124-6134.

Singh et al., "An Efficient Total Synthesis of Maleimycin", Tetrahedron 32, 1976, pp. 2379-2380.

Montero et al., "Reaction of Carbamoyl-S-benzylcarbodithiolate with Dipolarophilles", J. Org. Chem., 54, 1989, pp. 3664-3667.

P. ten Haken, "The Synthesis of 5,6-Dihydro-1,4-oxathiin-2,3-dicarboxylic Acid and Some Derivatives", J. Chem. Soc., vol. 7, 1970, pp. 1211-1213.

K. Alder et al., "Uber die Einführung con Substituenten in den Cyclopentadien-kern. I.", J. Lieb. Annalen d. Chem., vol. 524, 1936, pp. 145-180.

(Continued)

*Primary Examiner*—Joseph McKane
*Assistant Examiner*—Janet L Coppins
(74) *Attorney, Agent, or Firm*—Womble Carlyle Sandridge & Rice, PLLC

(57) ABSTRACT

The present invention relates to a novel compounds that can be used as anti-inflammatory, immunomodulatory and anti-proliferatory agents. In particular, the invention refers to new compounds which inhibit dihydroorotate dehydrogenase (DHODH), a process for their manufacture, pharmaceutical compositions containing them and to their use for the treatment and prevention of diseases, in particular their use in diseases where there is an advantage in inhibiting dihydroorotate dehyrogenase (DHODH).

12 Claims, 1 Drawing Sheet

OTHER PUBLICATIONS

Figure 1:
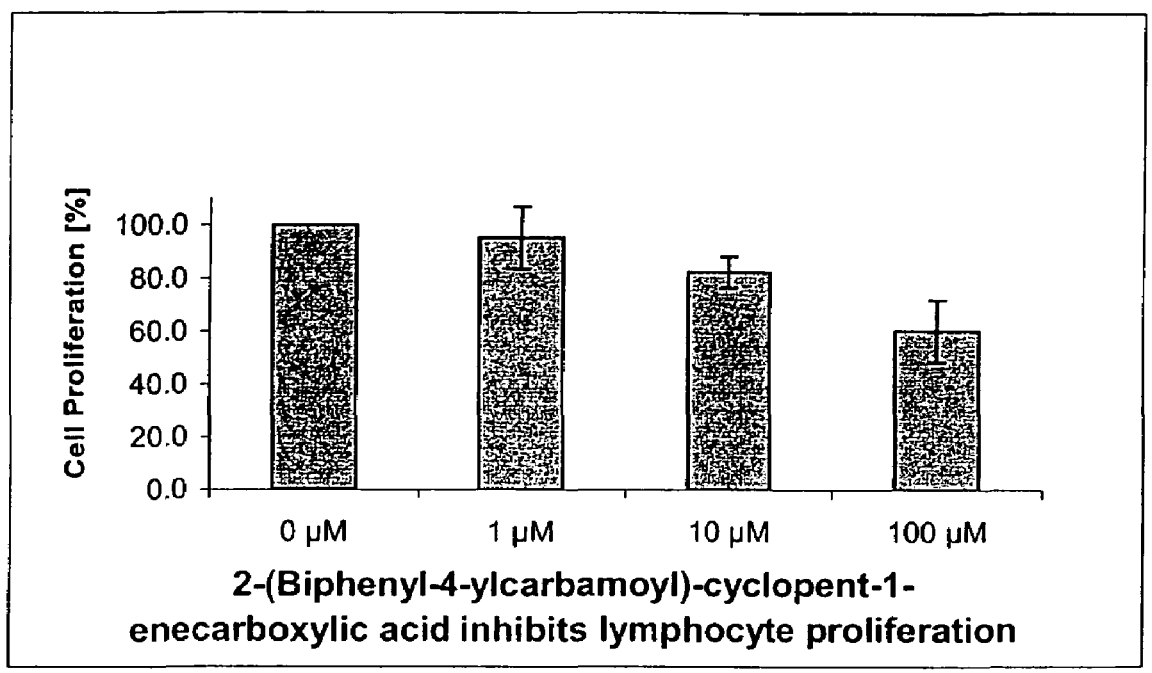

K. Alder et al., "Über die Dien-synthesen von 1,5,5-Trimethyl-cyclopentadien-1,3,α- und β-Camphylsäure mit Maleninsäure-anhydrid und Acetylen-dicarbonsäure", J. Lieb. Annalen d. Chem., vol. 543, 1940, pp. 56-78.

J.V. de Julián Ortiz et al., "Virtual Combinatorial Syntheses and Computational Screening of New Potential Anti-Herpes Compounds:", J. Med. Chem. 42, 1999, pp. 3308-3314.

G.W. Kabalka et al., "Suzuki coupling with ligandless palladium and potassium fluoride", Chem. Commun., 2001, p. 775.

A. Demeter, "The Influence of Aryl Substitution on the Photophysics of 1-Aryl-Fluorenones", Tetrahedron Letters, vol. 38, No. 29, 1997, pp. 5219-5222.

S. Nerdinger et al., "Directed ortho Metalation and Suzuki-Miyaura cross-coupling connections: regiospecific synthesis of all isometric chlorodihydroxybiphenyls for microbial degradation studies of PCBs", Chem. Commmun., 1999, pp. 2259-2260.

F.W. Sum et al., "Prodrugs of CL316243: A Selective $\beta_3$-Adrenergic Receptor Agponist For Treating Obesity and Diabetes", Bioorg. & Med. Chem. Letters, vol. 9, 1999, pp. 1921-1926.

Ada Rephaeli et al., "Prodrugs of Butyric Acid From Bench To Bedside: Synthetic Design, Mechanisms of Action, and Clinical Applications", Drug Development Research, vol. 50, 2000, pp. 379-391.

H. Ishikawa, Current Med. Chem. 6, 1999, pp. 575-597.

R.M. Scarborough et al., "Platelet Glycoprotein llb-llla Antagonists as Protypical Integrin Blockers: Novel Parenteral and Potential Oral Antithrombotic Agents", J. Med. Chem., vol. 43, No. 19, 2000, 3454-3473.

Matsui et al., "N-Substituted-Δ'-cyclopentene-1,2-dicarboxylic acid monoamides as herbicides", Mitsubishi Chem. Ind. Co. Ltd., vol. 84, No. 5, XP-002199075. 6001 Abstracts, 1976.

De Julian-Ortiz et al., "Virtual Combinatorial Syntheses and Computational Screening of New Potential Anti-Herpes Compounds", J. Med. Chem., 1999, No. 42, pp. 3308-3314.

Knecht et al., "Kinetics of inhibition of Human and Rat Dihydroorotate Dehdrogenase by Atovaquone, Lawsone Derivatives, Brequinar Sodium and Polyporic Acid", Chem. Biol. Interact, vol. 124, 2000, 61-76.

Jöckel et al., "Structural and Function comparison of Agents Intefering with Dihydroorotate, Succinate and NADH Oxidation of Rat Liver Mitochondria", Biochemical Pharmacology, vol. 26, 1998, 1053-1060.

* cited by examiner

COMPOUNDS AS ANTI-INFLAMMATORY, IMMUNOMODULATORY AND ANTI-PROLIFERATORY AGENTS

CONTINUING APPLICATION DATA

The present application is a Divisional of U.S. application ser. No. 10/193,526, filed on Jul. 9, 2002, now U.S. Pat. No. 7,176,241, which is a Continuation of PCT/EP01/07948, filed Jul. 10, 2001.

FIELD OF THE INVENTION

The present invention relates to novel compounds that can be used as antiinflammatory, immunomodulatory and anti-proliferatory agents. In particular the invention refers to new compounds which inhibit dihydroorotate dehydrogenase (DHODH), a process for their manufacture, pharmaceutical compositions containing them and to their use for the treatment and prevention of diseases, in particular their use in diseases where there is an advantage in inhibiting dihydroorotate dehydrogenase (DHODH).

BACKGROUND

Rheumatoid arthritis (RA) is a disease which is quite common especially among elder people. Its treatment with usual medications as for example non-steroid anti-inflammatory agents is not satisfactory. In view of the increasing ageing of the population, especially in the developed Western countries or in Japan the development of new medications for the treatment of RA is urgently required.

WO 99/38846 and EP 0 646 578 disclose compounds which are reported to be useful for treatment of RA.

A medicament against rheumatoid arthritis with a new mechanism of action, leflunomide, was recently put on the market by the company Aventis under the tradename ARAVA [EP 780128, WO 97/34600]. Leflunomide has immunomodulatory as well as anti-inflammatory properties [EP 217206, DE 2524929]. The mechanism of action is based upon the inhibition of dihydroorotate dehydrogenase (DHODH), an enzyme of the pyrimidine biosynthesis.

In the body, DHODH catalyzes the synthesis of pyrimidines, which are necessary for cell growth. An inhibition of DHODH inhibits the growth of (pathologically) fast proliferating cells, whereas cells which grow at normal speed may obtain their required pyrimidine bases from the normal metabolic cycle. The most important types of cells for the immuno response, the lymphocytes, use exclusively the synthesis of pyrimidines for their growth and react particularly sensitively to DHODH inhibition. Substances that inhibit the growth of lymphocytes are important medicaments for the treatment of auto-immuno diseases.

The DHODH inhibiting leflunomide (ARAVA) is the first medicament of this class of compounds (leflunomides) for the treatment of rheumatoid arthritis. WO 99/45926 is a further reference that discloses compounds which act as inhibitors of DHODH.

JP-A-50-121428 discloses N-substituted cyclopentene-1,2-dicarboxylic acid monoamides as herbicides and their syntheses. For example, N-(4-chlorophenyl)-1-cyclopentene-1,2-dicarboxylic acid monoamide is produced by reacting 1-cyclopentene-1,2-dicarboxylic anhydride with 4-chloroaniline.

In the Journal of Med. Chemistry, 1999, Vol. 42, pages 3308-3314, virtual combinatorial syntheses and computational screening of new potential Anti-Herpes compounds are described. In Table 3 on page 3313 experimental results regarding $IC_{50}$ and cytotoxicity are presented for 2-(2,3-difluorophenylcarbamoyl)-1-cyclopentene-1-carboxylic acid, 2-(2,6-difluorophenylcarbamoyl)-1-cyclopentene-1-carboxylic acid and 2-(2,3,4-trifluorophenyl-carbamoyl)-1-cyclopentene-1-carboxylic acid.

DE 3346814 and U.S. Pat. No. 4,661,630 disclose carboxylic acid amides. These compounds are useful for diseases attended with cerebral dysfunction and also have anti-ulcer, anti-asthma, anti-inflammatory and hypo-cholesterol activities.

In EP 0097056, JP 55157547, DE 2851379 and DE 2921002 tetrahydrophthalamic acid derivatives are described.

FIGURE

FIG. 1 shows the reduction of human lymphocyte cell proliferation caused by 2-(Biphenyl-4-ylcarbamoyl)-cyclopent-1-enecarboxylic acid used in a concentration of 100 μM.

DETAILED DESCRIPTION OF THE INVENTION

It is an object of the present invention to provide alternative effective agents which can be used for the treatment of diseases which require the inhibition of DHODH.

Accordingly, a novel class of compounds with an inhibitory effect on DHODH, in particular human DHODH, was found.

The present invention is therefore directed to compounds of the general formula (I)

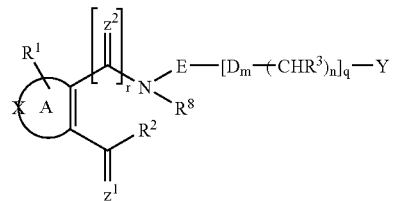

or salts thereof,
wherein

A is a non-aromatic ring system containing five carbon atoms, wherein the ring system comprises at least one double bond and wherein one or more of the carbon atoms in the ring can be replaced by a group X, wherein X is selected from the group consisting of S, O, N, $NR^4$, SO or $SO_2$, and wherein one or more of the carbon atoms of the ring can carry a substituent $R^1$;

D is O, S, $SO_2$, $NR^4$, or $CH_2$;

$Z^1$ and $Z^2$ are independent from each other O, S, or $NR^5$;

$R^1$ is independently H, halogen, haloalkyl, haloalkyloxy or alkyl;

$R^2$ is H, $OR^6$, or $NHR^7$;

$R^3$ is H, alkyl, cycloalkyl, aryl, arylalkyl, alkoxy, O-aryl; O-cycloalkyl, halogen, aminoalkyl, alkylamino, hydroxylamino, hydroxylalkyl, haloalkyl, haloalkyloxy, heteroaryl, alkylthio, S-aryl, or S-cycloalkyl;

$R^4$ is H, alkyl, cycloalkyl, aryl, or heteroaryl;

$R^5$ is H, OH, alkoxy, O-aryl, alkyl, or aryl;

$R^6$ is H, alkyl, cycloalkyl, aryl, heteroaryl, arylalkyl, alkylaryl, alkoxyalkyl, acylmethyl, (acyloxy)alkyl, non-symmetrical (acyloxy)alkyldiester, or dialkylphosphate;

$R^7$ is H, alkyl, aryl, alkoxy, O-aryl, cycloalkyl, or O-cycloalkyl;

$R^8$ is hydrogen or alkyl;

E is an alkyl or cycloalkyl group or a monocyclic or polycyclic substituted or unsubstituted ring system which may contain one or more groups X and which contains at least one aromatic ring;

Y is hydrogen, halogen, haloalkyl, haloalkyloxy, alkyl, cycloalkyl, a monocyclic or polycyclic substituted or unsubstituted ring system which may contain one or more groups X and which contains at least one aromatic ring or

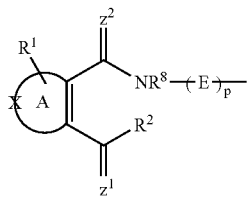

m is 0 or 1;
n is 0 or 1;
p is 0 or 1;
r is 0 or 1; and
q is 0 to 10;

with the provison that when ring A is an unsubstituted carbocycle containing five carbon atoms and one double bond between the $CZ^1$ and $CZ^2$-substituents, wherein $Z^1=Z^2=O$, and $R^2=OH$, and r=1, the following compounds are excluded:

q=0; Y=hydrogen; E=phenylene or naphthylene, phenylene substituted with one or two chlorine atoms or with 2-methyl, 4-methyl, 4-methoxy, 4-ethoxy, 2,6-diethyl, 2-chloro-4-methyl, 4-bromo, 4-cyano, 2,3-difluoro, 2,6-difluoro, 2,3,4-trifluoro;

q=0; Y=phenyl; E=phenylene;

q=1; m=1; n=1; $R^3$=H; E=phenylene; Y=4-chloro-phenyl; D=O, S;

q=1; m=1; n=1; $R^3$=H; E=phenylene; Y=4-phenyl; D=O.

The present invention is also directed to compounds of the general formula (Ia)

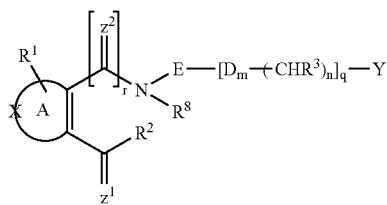

and salts thereof,
wherein

A is a non-aromatic ring system containing 4, 6, 7 or 8 carbon atoms, wherein the ring system comprises at least one double bond and wherein one or more of the carbon atoms in the ring can be replaced by a group X, wherein X is selected from the group consisting of S, O, N, $NR^4$, SO or $SO_2$, and wherein one or more of the carbon atoms of the ring can carry a substituent $R^1$;

D is O, S, $SO_2$, $NR^4$, or $CH_2$;

$Z^1$ and $Z^2$ are independent from each other O, S, or $NR^5$;

$R^1$ is independently H, halogen, haloalkyl, haloalkyloxy or alkyl;

$R^2$ is H, or $OR^6$;

$R^3$ is H, alkyl, cycloalkyl, aryl, alkoxy, O-aryl; O-cycloalkyl, halogen, aminoalkyl, alkylamino, hydroxylamino, hydroxylalkyl, haloalkyloxy, heteroaryl, alkylthio, S-aryl; S-cycloalkyl, arylalkyl, or haloalkyl;

$R^4$ is H, alkyl, cycloalkyl, aryl or heteroaryl;

$R^5$ is H, OH, alkoxy, O-aryl, alkyl or aryl;

$R^6$ is H, alkyl, cycloalkyl, aryl, arylalkyl, heteroaryl, alkylaryl, alkoxyalkyl, acylmethyl, (acyloxy)alkyl, non-symmetrical (acyloxy)alkyldiester, or dialkylphosphate;

$R^8$ is hydrogen or alkyl;

E is an alkyl or cycloalkyl group or a monocyclic or polycyclic substituted or unsubstituted ring system which may contain one or more groups X and which contains at least one aromatic ring;

Y is a monocyclic or polycyclic substituted or unsubstituted ring system which may contain one or more groups X and which contains at least one aromatic ring or

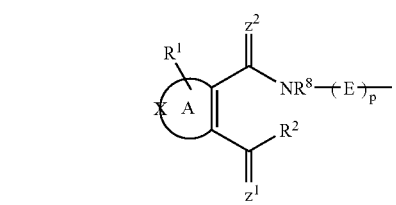

m is 0 or 1;
n is 0 or 1;
p is 0 or 1;
r is 0 or 1; and
q is 0 to 10;

An alkyl group, if not stated otherwise, is preferably a linear or branched chain of 1 to 6 carbon atoms, preferably a methyl, ethyl, propyl, isopropyl, butyl, t-butyl, isobutyl, pentyl or hexyl group, a methyl, ethyl, isopropyl or t-butyl group being most preferred. The term "alkyl", unless otherwise noted, is also meant to include those derivatives of alkyl defined in more detail below as "unsaturated alkyl". An unsaturated alkyl group is one having one or more double bonds or triple bonds, preferably vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The alkyl group in the compounds of formula (I) or formula (Ia) can optionally be substituted by one or more substituents R', preferably by halogen.

R' is independently H, —$CO_2R''$, —CONHR", —CR"O, —$SO_2NR''$, —NR"—CO-haloalkyl, —$NO_2$—NR"—$SO_2$-haloalkyl, —NR"—$SO_2$-alkyl, —$SO_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R" is independently hydrogen, haloalkyl, hydroxyalkyl, alkyl, cycloalkyl, aryl, heteroaryl or aminoalkyl;

An cycloalkyl group denotes a non-aromatic ring system containing 3 to 8 carbon atoms, wherein one or more of the carbon atoms in the ring can be replaced by a group X, X being as defined above.

An alkoxy group denotes an O-alkyl group, the alkyl group being as defined above.

An alkylthio group denotes an S-alkyl group, the alkyl group being as defined above.

A hydroxyalkyl group denotes an HO-alkyl group, the alkyl group being as defined above.

An haloalkyl group denotes an alkyl group which is substituted by one to five preferably three halogen atoms, the alkyl group being as defined above; a $CF_3$ being preferred.

An haloalkyloxy group denotes an alkoxy group which is substituted by one to five preferably three halogen atoms, the alkoxy group being as defined above; a $OCF_3$ being preferred.

A hydroxyalkylamino group denotes an $(HO\text{-alkyl})_2$—N-group or HO-alkyl-NH-group, the alkyl group being as defined above.

An alkylamino group denotes an HN-alkyl or N-dialkyl group, the alkyl group being as defined above.

An aminoalkyl group denotes an $H_2N$-alkyl, monoalkylaminoalkyl, or dialkylaminoalkyl group, the alkyl group being as defined above.

A halogen group is chlorine, bromine, fluorine or iodine, fluorine being preferred.

An aryl group preferably denotes an aromatic group having 5 to 15 carbon atoms, in particular a phenyl group. This aryl group can optionally be substituted by one or more substituents R', where R' is as defined above, preferably by haloalkyloxy.

An arylalkyl group denotes an alky group which is substituted by one to three preferably one aryl groups, the alkyl and aryl group being as defined above.

A heteroaryl group denotes a 5- or 6-membered heterocyclic group which contains at least one heteroatom bike O, N, S. This heterocyclic group can be fused to another ring. For example, this group can be selected from an oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, benzo-[b]-furanyl, benzo[b]thiophenyl, benzimidazolyl, benzothiazolyl, quinazolinyl, quinoxazolinyl, or preferably isoxazol-3-yl, isoxazol-4-yl, isoxazol-5-yl, quinolinyl, tetrahydroquinolinyl, isoquinolinyl, tetrahydroisoquinolinyl group. This heterocyclic group can optionally be substituted by one or more substituents R', where R' is as defined above.

The meaning of E includes optional by one or more substituents R substituted alkyl groups, wherein alkyl is defined as above or as a cycloalkyl group optionally substituted by one or more substituents R' such as cyclopropyl, cyclobutyl, cyclopentyl, cyclohexyl, cycloheptyl, cyclooctyl or carbocyclic aromatic groups such as phenyl, 1-naphthyl, 2-naphthyl, 2-naphthyl, anthracenyl, in particular 1-anthracenyl and 2-anthracenyl, and heterocyclic aromatic groups such as N-imidazolyl, 2-imidazolyl, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 4-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl. E includes also fused polycyclic aromatic ring systems such as 9H-thioxanthene-10,10-dioxide in which a carbocyclic aromatic ring or heteroaryl ring is fused to one or more other heteroaryl ring.

The invention also provides a pharmaceutical composition comprising a compound of formula (I) including the compounds excluded by the disclaimer in claim 1 or a compound of formula (Ia), in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs such as those described below in the present application.

In another aspect, the present invention also provides a method for the treatment or prophylaxis of a condition where there is an advantage in inhibiting dihydroorotate dehydrogenase (DHODH) which comprises the administration of an effective amount of a compound of formula (I) or of formula (Ia) and physiologically acceptable salts or physiologically functional derivatives thereof.

The invention is also directed to the use of compounds of the formula (I) or of formula (Ia) and of their pharmacologically tolerable salts or physiologically functional derivatives for the production of a medicament for the prevention and treatment of diseases, where inhibition of the pyrimidine biosynthesis is of benefit.

In addition, the present invention provides methods for preparing the compounds of the invention such as desired amides of the formula (I) or of the formula (Ia).

A first method for synthesis of amides of formula (I) or of the formula (Ia) comprises the step of reacting an acid anhydride of formula (II) with an amine of the formula (III).

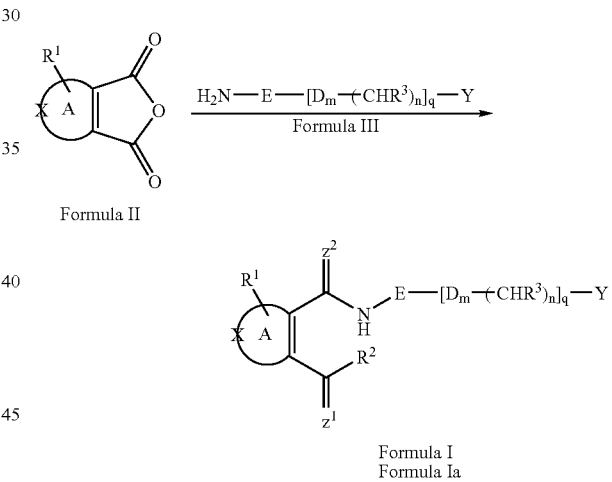

Formula II

Formula I
Formula Ia

A second method of the invention for preparing the compounds of formula (I) or of formula (Ia) comprises the step of reacting an amine of the formula (IV) with an aryl-boronic acid of the general formula (V) or formula (Va) $(HO)_2B$—E—$[D_m$—$(CHR^3)_n]_q$—Y [M. P. Winters, Tetrahedron Lett, 39, (1998), 2933-2936].

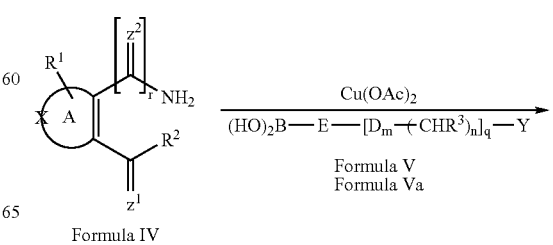

Formula IV

Formula V
Formula Va

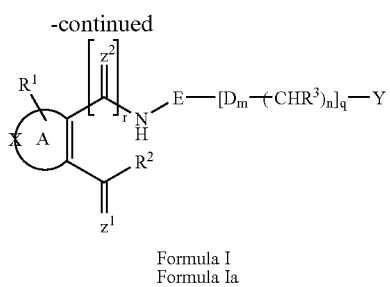

Formula I
Formula Ia

A third method of the invention for preparing the compounds of formula (I) or of formula (Ia) comprises the step of reacting an halogen derivative of the formula (VI) with an arylboronic acid of the general formula (VII) or formula (VIIa) [N. E. Leadbeater, S. M. Resouly, Tetrahedron, 55, 1999, 11889-11894]. Q is a halogen group such as chlorine, bromine, fluorine or iodine, bromine being preferred.

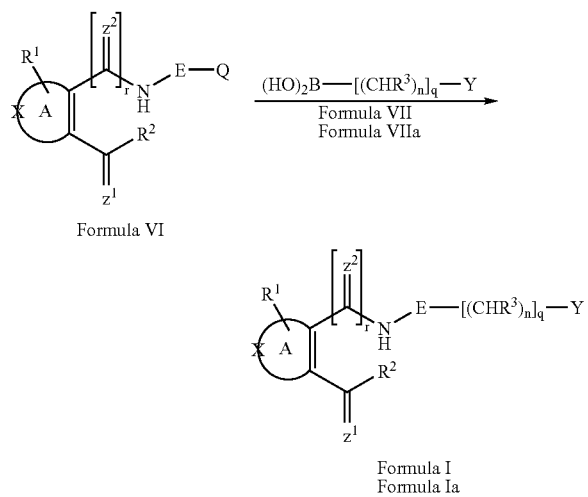

Formula I
Formula Ia

A fourth method of the invention for preparing the compounds of formula (I) [r=0] or of formula (Ia) [r=0] comprises the step of reacting an amine of the formula (III) with a compound of the formula (VIII) [Bew, J. Chem. Soc. 1955, 1775-1777].

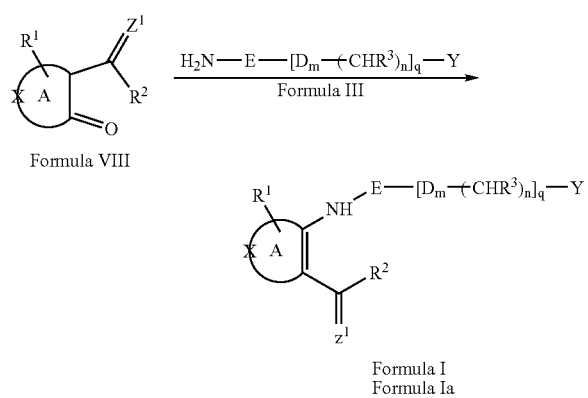

Formula I
Formula Ia

In the compounds of formula (I) the non-aromatic ring system A contains 5 carbon atoms. In the compounds of formula (Ia) the non-aromatic ring system A contains 4, 6, 7 or 8, preferably 6 carbon atoms. The ring system A comprises at least one double bond which is located between the $CZ^1$ and $CZ^2$-substituents as depicted in formula (I) or in formula (Ia). In preferred embodiments, the compounds of the present invention contain only this double bond. In case of two or more double bonds, these double bonds are not-conjugated. One or more of the carbon atoms in the ring system A can be replaced by a group X, wherein X is selected from the group consisting of S, O, N, $NR^4$, SO or $SO_2$. In one preferred embodiment, one carbon atom is replaced by a group X=S or X=O. In a more preferred embodiment, none of the carbon atoms is replaced by a group X.

In another preferred embodiments, in the compounds of formula (I) A is 1-cyclopenten-1,2-diyl, 2,5-dihydro-thiophene-3,4-diyl, 2,5-dihydro-furan-3,4-diyl, 2,5-dihydro-1H-pyrrole-3,4-diyl, 2,5-dihydro-1-methyl-pyrrole-3,4-diyl, 2,5-dihydro-1-ethyl-pyrrole-3,4-diyl, 2,5-dihydro-1-acetyl-pyrrole-3,4-diyl, 2,5-dihydro-1-methyl-sulfonyl-pyrrole-3,4-diyl.

In another preferred embodiments, in the compounds of formula (Ia) A is 1-cyclobuten-1,2-diyl, 1-cyclohexen-1,2-diyl, 1-cyclohepten-1,2-diyl or 1-cycloocten-1,2-diyl.

In the compounds of formula (I) or of formula (Ia) D is O, S, $SO_2$, $NR^4$, or $CH_2$. D is preferably S or more preferably O, when m=1.

In other preferred embodiments, in the compounds of formula (I) m and q are zero and Y is hydrogen, halogen, haloalkyl, haloalkyloxy, alkyl, cycloalkyl or E, preferably F, $CF_3$, $OCF_3$, an optionally by one or more substituents R substituted phenyl or more preferably an optionally by one or more F, Cl, methoxy, $CF_3$, or $OCF_3$ substituted phenyl.

In the compounds of formula (I) or of formula (Ia) $R^1$ is independently H, halogen, haloalkyl, haloalkyloxy or alkyl, preferably $R^1$ is H.

In the compounds of formula (I) $R^2$ is H, $OR^6$, or $NHR^7$, preferably OH or $OR^6$. In the compounds of formula (Ia) $R^2$ is H, or $OR^6$, preferably OH or $OR^6$.

In preferred embodiments, in the compounds of formula (I) or of formula (Ia) $R^6$ is benzoyloxymethyl, isobutyryloxymethyl, 4-aminobutyryloxymethyl, butyryloxymethyl, 1-(butyryloxy)ethyl, 1-(butyryloxy)-2,2-dimethylpropyl, 1-diethylphosphonooxyethyl, 2-(2-methoxyethoxy)-acetyloxymethyl, p-aminobenzoylmethyl, nicotinyloxymethyl, pivaloyloxymethyl, glutaryloxymethyl, [2-(2-methoxyethoxy)ethoxy]-acetyloxymethyl, 2-(morpholine-4-yl)-ethyl, 1-diethylphosphonooxymethyl.

In the compounds of formula (I) or of formula (Ia) $R^3$ is is H, alkyl, cycloalkyl, aryl, alkoxy, O-aryl; O-cycloalkyl, halogen, aminoalkyl, akylamino, hydroxylamino, haloalkyl, hydroxylalkyl, haloalkyloxy, heteroaryl, alkylthio, S-aryl; S-cycloalkyl, arylalkyl, preferably H;

$R^4$ in formula (I) or in formula (Ia) is H, alkyl, cycloalkyl, aryl or heteroaryl.

In formula (I) or in formula (Ia) $R^8$ is H or alkyl, preferably H or methyl.

In formula (I) or in formula (Ia) $Z^1$ and $Z^2$ are independent from each other O, S, or $NR^5$, preferably both are O.

In formula (I) Y is hydrogen, halogen, alkyl, substituted or unsubstituted cycloalkyl, substituted or unsubstituted E, substituted or unsubstituted O—E, substituted or unsubstituted O-alkylaryl, substituted or unsubstituted O-arylalkyl; in case of said substitution, substitution of one or more hydrogen atoms of the alkyl-, cycloalkyl-, or aryl-groups by halogens are preferred. Y can also be

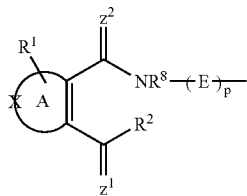

wherein A, X, $R^1$, $R^2$, $R^8$, $Z^1$, $Z^2$ and p have the meaning as defined above. Preferably Y is E and more preferably Y is an optionally substituted phenyl.

In formula (Ia) Y is E, preferably Y is an optionally substituted phenyl.

In formula (I) or in formula (Ia) E is an alkyl or cycloalkyl group which is optionally substituted by one or more substituents R', or E is a monocyclic or polycyclic substituted or unsubstituted ring system which contains at least one aromatic ring and which may also contain one or more groups X selected from S, O, N, $NR^4$, SO or $SO_2$. In preferred embodiments, E is a monocyclic aromatic ring or an aromatic bicyclic or tricyclic ring system, or cycloalkyl. In case of substitutions of carbon atoms in the ring system, preferably one, two or three carbon atoms are replaced by a group X as defined above.

In formula (I) or in formula (Ia) E is preferably an optionally by one or more substituents $R^1$ substituted phenyl, 1-naphtyl, 2-naphtyl, 1-anthracyl and 2-anthracyl.

In a preferred embodiment of the present invention in compounds of formula (I) or of formula (Ia) E is an optionally by one or more substituents $R^1$ substituted phenyl, or an optionally by one or more substituents $R^1$ substituted cycloalkyl.

In formula (I) or in formula (Ia) preferred substituents R' are nitro, halogen, alkoxy, haloalkyl, haloalkyloxy, heteroaryl, alkyl or aryl, more preferably R' is Br, F, Cl, $CF_3$, $OCF_3$, or methoxy.

In formula (I) or in formula (Ia) preferred heteroaryl groups are imidazoyl, thienyl, furanyl, pyridyl, pyrimidyl, pyranyl, pyrazolyl, pyrazinyl, thiazolyl, or oxazolyl.

In particular preferred embodiments of the invention, in compounds of formula (I), q=0, and r=1, and A is a carbocyclic non-aromatic ring system, Y is H or F, or E is phenyl which is either unsubstituted or substituted with Cl, F and/or $CF_3$ or $OCF_3$.

In another particularly preferred embodiment of the invention, in compounds of formula (I) or in formula (Ia), q=0, and r=1, or A is a carbocyclic non-aromatic ring system, and E and Y are substituted or unsubstituted phenylene and phenyl, respectively.

In further particularly preferred embodiment, in compounds of formula (I) or in formula (Ia), D=O (thus m=1), $R^3$ is H (thus n=1), q=1 or 2, and r=1, E is phenylene which is either unsubstituted or substituted with Cl, F and/or $CF_3$ or $OCF_3$, and Y is phenyl which is also either unsubstituted or substituted with Cl, F and/or $CF_3$ or $OCF_3$, or A is a carbocyclic non-aromatic ring system.

In further particularly preferred embodiment, in compounds of formula (I) or in formula (Ia), D=O (thus m=1), n=0, q=1 or 2, and r=1, E is phenylene which is either unsubstituted or substituted with Cl, F and/or $CF_3$ or $OCF_3$, and Y is phenyl which is also either unsubstituted or substituted with Cl, F and/or $CF_3$ or $OCF_3$, or A is a carbocyclic non-aromatic ring system.

In further particularly preferred embodiment, in compounds of formula (I) or in formula (Ia), D=S (thus m=1), n=0, q=1 or 2, and r=1, E is phenylene which is either unsubstituted or substituted with Cl, F and/or $CF_3$ or $OCF_3$, and Y is phenyl which is also either unsubstituted or substituted with Cl, F and/or $CF_3$ or $OCF_3$, or A is a carbocyclic non-aromatic ring system.

In particular preferred embodiments of the invention, in compounds of formula (I), q=0, and r=1, or A is a non-aromatic ring system, wherein one carbon atom is replaced by O, or Y is H or F, and E is phenyl which is either unsubstituted or substituted with Cl, F and/or $CF_3$ or $OCF_3$.

In another particularly preferred embodiment of the invention, in compounds of formula (I) or in formula (Ia), q=0, and r=1, and A is a non-aromatic ring system, wherein one carbon atom is replaced by O, or E and Y are substituted or unsubstituted phenylene and phenyl, respectively.

In further particularly preferred embodiment, in compounds of formula (I) or in formula (Ia), D=O (thus m=1), $R^3$ is H (thus n=1), q=1 or 2, and r=1, E is phenylene which is either unsubstituted or substituted with Cl, F and/or $CF_3$ or $OCF_3$, and Y is phenyl which is also either unsubstituted or substituted with Cl, F and/or $CF_3$ or $OCF_3$, or A is a non-aromatic ring system, wherein one carbon atom is replaced by O.

In further particularly preferred embodiment, in compounds of formula (I) or in formula (Ia), D=O (thus m=1), n=0, q=1 or 2, and r=1, E is phenylene which is either unsubstituted or substituted with Cl, F and/or $CF_3$ or $OCF_3$, and Y is phenyl which is also either unsubstituted or substituted with Cl, F and/or $CF_3$ or $OCF_3$, or A is a non-aromatic ring system, wherein one carbon atom is replaced by O.

In further particularly preferred embodiment, in compounds of formula (I) or in formula (Ia), D=S (thus m=1), n=0, q=1 or 2, and r=1, E is phenylene which is either unsubstituted or substituted with Cl, F and/or $CF_3$ or $OCF_3$, and Y is phenyl which is also either unsubstituted or substituted with Cl, F and/or $CF_3$ or $OCF_3$, or A is a non-aromatic ring system, wherein one carbon atom is replaced by O.

In particular preferred embodiments of the invention, in compounds of formula (I), q=0, and r=1, or A is a non-aromatic ring system, wherein one carbon atom is replaced by S, or Y is H or F, and E is phenyl which is either unsubstituted or substituted with Cl, F and/or $CF_3$ or $OCF_3$.

In another particularly preferred embodiment of the invention, in compounds of formula (I) or in formula (Ia), q=0, and r=1, and A is a non-aromatic ring system, wherein one carbon atom is replaced by S, or E and Y are substituted or unsubstituted phenylene and phenyl, respectively.

In further particularly preferred embodiment, in compounds of formula (I) or in formula (Ia), D=O (thus m=1), $R^3$ is H (thus n=1), q=1 or 2, and r=1, E is phenylene which is either unsubstituted or substituted with Cl, F and/or $CF_3$ or $OCF_3$, and Y is phenyl which is also either unsubstituted or substituted with Cl, F and/or $CF_3$ or $OCF_3$, or A is a non-aromatic ring system, wherein one carbon atom is replaced by S.

In further particularly preferred embodiment, in compounds of formula (I) or in formula (Ia), D=O (thus m=1), n=0, q=1 or 2, and r=1, E is phenylene which is either unsubstituted or substituted with Cl, F and/or $CF_3$ or $OCF_3$, and Y is phenyl which is also either unsubstituted or substituted with Cl, F and/or $CF_3$ or $OCF_3$, or A is a non-aromatic ring system, wherein one carbon atom is replaced by S.

In further particularly preferred embodiment, in compounds of formula (I) or in formula (Ia), D=S (thus m=1), n=0, q=1 or 2, and r=1, E is phenylene which is either unsubstituted or substituted with Cl, F and/or CF$_3$ or OCF$_3$, and Y is phenyl which is also either unsubstituted or substituted with Cl, F and/or CF$_3$ or OCF$_3$, or A is a non-aromatic ring system, wherein one carbon atom is replaced by S.

In formula (I) q is 0 to 10, preferably q is 0, 1 or 2. If q is 1 and n is 0 or 1, D is preferably 0 (thus m=1) and r=1.

Preferred compounds of the present invention are: 2-(Biphenyl-4-ylcarbamoyl)-cyclopent-1-enecarboxylic acid; 2-(3-Trifluoromethyl-phenyl-carbamoyl)-cyclopent-1-enecarboxylic acid, 2-(Benzhydryl-carbamoyl)-cyclopent-1-ene-carboxylic acid; 2-(4-Benzyloxy-phenylcarbamoyl)-cyclopent-1-enecarboxylic acid; 2-(3-Nitro-phenylcarbamoyl)-cyclopent-1-enecarboxylic acid; 2-(10,10-Dioxo-9,10-dihydro-10λ$^6$-thioxanthen-2-ylcarbamoyl)-cyclopent-1-enecarboxylic acid; 2-(2-Trifluoro-methoxy-benzylcarbamoyl)-cyclopent-1-enecarboxylic acid; 2-(3-Trifluoromethoxy-benzylcarbamoyl)-cyclopent-1-enecarboxylic acid; 2-Methyl-4-(4-trifluoromethyl-benzylcarbamoyl)-pentanoic acid; 4-(3-Fluoro-benzylcarbamoyl)-2-methyl-pentanoic acid; 2-Methyl-4-[4-(4-nitro-benzenesulfonyl)-phenylcarbamoyl]-pentanoic acid; 2-[N'-(Bi-phenyl-4-carbonyl)-hydrazinocarbonyl]-cyclopent-1-enecarboxylic acid; 2-[4-(4-Methoxy-phenylamino)-phenylcarbamoyl]-cyclopent-1-enecarboxylic acid; 2-(3-Phenoxy-phenyl-carbamoyl)-cyclopent-1-enecarboxylic acid; 3-(Biphenyl-4-ylcarbamoyl)-acrylic acid; 2-Phenylcarbamoyl-cyclopent-1-enecarboxylic acid; 2-(4-Trifluoromethyl-phenyl-carbamoyl)-cyclopent-1-enecarboxylic acid; 2-(Methyl-phenyl-carbamoyl)-cyclopent-1-enecarboxylic acid; 4-Hydroxy-6-(4-trifluoromethyl-phenylcarbamoyl)-pyridine-2-carboxylic acid; 2-(2-Ethoxy-phenylcarbamoyl)-cyclopent-1-enecarboxylic acid; 2-(4-Nitro-3-trifluoromethyl-phenylcarbamoyl)-cyclopent-1-enecarboxylic acid; 2-(2-Methoxy-phenylcarbamoyl)-cyclopent-1-enecarboxylic acid; 6-Nitro-N-(4-trifluoro-methyl-phenyl)-phthalamic acid; 2-(3,5-Bis-trifluoromethyl-phenylcarbamoyl)-cyclopent-1-enecarboxylic acid; 3-[(2-Carboxy-cyclopent-1-enecarbonyl)-amino]-5-nitro-benzoic acid; 2-(3-Methanesulfonyl-phenylcarbamoyl)-cyclopent-1-enecarboxylic acid; 2-(4-Trifluoromethyl-benzylcarbamoyl)-cyclopent-1-enecarboxylic acid; 2-(3-Fluoro-5-tri-fluoromethyl-benzylcarbamoyl)-cyclopent-1-enecarboxylic acid; 2-(2-Trifluoromethyl-benzylcarbamoyl)-cyclopent-1-enecarboxylic acid; 2-(3-Trifluoromethyl-benzyl-carbamoyl)-cyclopent-1-enecarboxylic acid; 2-(3,5-Bis-trifluoromethyl-benzylcarbamoyl)-cyclopent-1-enecarboxylic acid; 2-(4-Trifluoromethyl-phenylcarbamoyl)-terephthalic acid; 4-[(2-Carboxy-cyclopent 1-enecarbonyl)-amino]-phthalic acid; 2-(4-Acetylamino-phenyl-carbamoyl)-cyclopent-1-enecarboxylic acid; 2-(3-Acetyl-phenylcarbamoyl)-cyclopent-1-enecarboxylic acid; 2-(4-Methoxy-2-nitro-phenylcarbamoyl)-cyclopent-1-enecarboxylic acid; 2-(2-Amino-5-trifluoromethyl-phenylcarbamoyl)-cyclopent-1-enecarboxylic acid; 2-(2,3,4-Trifluoro-phenylcarbamoyl)-cyclopent-1-enecarboxylic acid; 2-(2,3,4,5-Tetra-fluoro-phenylcarbamoyl)-cyclopent-1-enecarboxylic acid; 2-Pentafluorophenylcarbamoyl-cyclopent-1-enecarboxylic acid; 2-(2,4-Difluoro-phenylcarbamoyl)-cyclopent-1-enecarboxylic acid; 2-(2,3,4,6-Tetrafluoro-phenylcarbamoyl)-cyclopent-1-enecarboxylic acid; 2-(2,3,5,6-Tetrafluoro-phenylcarbamoyl)-cyclopent-1-enecarboxylic acid; 2-(2-Nitro-4-tri-fluoromethyl-phenyl)-cyclopent-1-enecarboxylic acid; 2-(2,4-Bis-trifluoro-methyl-phenyl-carbamoyl)-cyclopent-1-enecarboxylic acid; 2-(4-Nitro-2-trifluoromethyl-phenylcarbamoyl)-cyclopent-1-enecarboxylic acid; 2-(2,3,5,6-Tetrafluoro-4-trifluoro-methyl-phenylcarbmoyl)-cyclopent-1-enecarboxylic acid; 2-(2,4,6-Trifluoro-phenyl-carbamoyl)-cyclopent-1-enecarboxylic acid; 2-(2,6-Difluoro-phenylcarbamoyl)-cyclopent-1-enecarboxylic acid; 2-(2,3-Difluoro-phenylcarbamoyl)-cyclopent-1-enecarboxylic acid; 2-(4-Trifluoromethyl-phenylcarbamoyl)-cyclopropanecarboxylic acid; 3-(4-Trifluoro-methyl-phenylcarbamoyl)-pyrazine-2-carboxylic acid; 3-(4-Trifluoromethyl-phenyl-carbamoyl)-5,6-dihydro-[1,4]dithiine-2-carboxylic acid; 3-(4-Trifluoromethyl-phenyl-carbmoyl)-7-oxa-bicyclo[2.2.1]hept-5-ene-2-carboxylic acid; 3-(4-Trifluoromethyl-phenylcarbamoyl)-isonicotinic acid; 2-(4-Trifluoromethyl-phenylcarbamoyl)-cyclobutane-carboxylic acid; 2-[4-(2,6-Dichloro-benzyloxy)-phenylcarbamoyl]-cyclopent-1-ene-carboxylic acid; 2-(4-Phenoxy-phenylcarbamoyl)-cyclopent-1-enecarboxylic acid; 2-[4-(Pyrimidin-2-ylsulfamoyl)-phenylcarbamoyl]-cyclopent-1-enecarboxylic acid; 2-[4-(5-Methyl-isoxazol-3-ylsufamoyl)-phenylcarbamoyl]-cyclopent-1-enecarboxylic acid; 2-(3-Benzyloxy-phenylcarbamoyl)-cyclopent-1-enecarboxylic acid; 2-(4-Benzene-sulfonyl-phenylcarbamoyl)-cyclopent-1-enecarboxylic acid; 2-[4-(2 4-Dichloro-phenoxy)-phenyl-carbamoyl]-cyclopent-1-enecarboxylic acid; 2-[4-(2,6-Dichloro-benzyloxy)-phenyl]-5,6-dihydro-4H-cyclopenta[c]pyrrole-1,3-dione; 2-[4-(4-Fluoro-benzyloxy)-phenylcarbamoyl]-cyclopent-1-enecarboxylic acid; 2-(4-Heptyl-phenylcarbamoyl)-cyclopent-1-enecarboxylic acid; 2-(4-Styryl-phenylcarbamoyl)-cyclopent-1-enecarboxylic acid; 2-(4-m-Tolylsulfanyl-phenylcarbamoyl)-cyclopent-1-enecarboxylic acid; 2-(2,3,5,6,2',3',4',5',6'-Nonafluoro-biphenyl-4-ylcarbamoyl)-cyclopent-1-enecarboxylic acid; 2-(4-Benzyloxy-3,5-dibromo-phenylcarbamoyl)-cyclopent-1-enecarboxylic acid; 2-(4-Phenylamino-phenylcarbamoyl)-cyclopent-1-enecarboxylic acid; 2-(Biphenyl-4-yl-carbamoyl)-cyclohexanecarboxylic acid; 6-(Biphenyl-4-ylcarbamoyl)-cyclohex-3-ene-carboxylic acid; 2-(2'-Fluoro-biphenyl-4-ylcarbamoyl)-cyclopent-1-enecarboxylic acid; 2-(2'-Trifluoromethoxy-biphenyl-4-ylcarbamoyl)-cyclopent-1-enecarboxylic acid; 2-(2'-Chloro-biphenyl-3-ylcarbamoyl)-cyclopent-1-enecarboxylic acid; 2-(2-(4'-Chloro-bi-phenyl-3-ylcarbamoyl)-cyclopent-1-enecarboxylic acid; 2-(2',4'-Difluoro-biphenyl-4-yl-carbamoyl)-cyclopent-1-enecarboxylic acid; 2-[3,5-Dibromo-4-(3,5-difluoro-benzyloxy)-phenylcarbamoyl]-cyclopent-1-enecarboxylic acid; 2-[4-(3,5-Difluoro-benzyloxy)-phenyl-carbamoyl]-cyclopent-1-enecarboxylic acid; 2-(3'-Acetyl-biphenyl-4-ylcarbamoyl)-cyclo-pent-1-enecarboxylic acid; 2-[3,5-Dibromo-4-(2,6-difluoro-benzyloxy)-phenylcarbamoyl]-cyclopent-1-enecarboxylic acid; 2-(2'-Ethoxy-biphenyl-4-ylcarbamoyl)-cyclopent-1-ene-carboxylic acid; 2-(2'-Methoxy-biphenyl-4-ylcarbamoyl)-cyclopent-1-enecarboxylic acid; 2-(3'-Ethoxy-biphenyl-4-ylcarbamoyl)-cyclopent-1-enecarboxylic acid; 2-(3',4'-Di-methoxy-biphenyl-4-ylcarbamoyl)-cyclopent-1-enecarboxylic acid; 2-(2',4'-Dimethoxy-bi-phenyl-4-ylcarbamoyl)-cyclopent-1-enecarboxylic acid; 2-(4'-Phenoxy-bi-phenyl-4-yl-carbamoyl)-cyclopent-1-enecarboxylic acid; 2-(3'-Trifluoromethoxy-biphenyl-4-yl-carbamoyl)-cyclo-pent-1-enecarboxylic acid; 2-(4'-Trifluoromethoxy-biphe-nyl-4-yl-carbamoyl)-cyclopent-1-enecarboxylic acid; 2-[3,5-Dibromo-4-(2,3-difluoro-benzyloxy)-phenylcarbamoyl]-cyclopent-1-enecarboxylic acid; 2-[4-(2,3-Difluoro-benzyloxy)-phenylcarbamoyl]-cyclopent-1-enecarboxylic acid; 2-[4-(2,6-Difluoro-benzyloxy)-phenylcarbamoyl]-cyclopent-1-enecarboxylic acid; 2-(4'-Methylsulfanyl-biphe-nyl-4-yl-carbamoyl)-cyclopent-1-enecarboxylic acid; 2-[4-(5-Chloro-thiophen-2-yl)-phenyl-carbamoyl]-cyclopent-1-enecarboxylic acid; 2-(4-Thiophen-2-yl-phenylcarbamoyl)-cyclo-pent-1-enecarboxylic acid; 2-(4-Benzofuran-2-yl-phenylcarbamoyl)-cyclopent-1-ene-carboxylic acid; 2-(4-

Benzo[b]thiophen-2-yl-phenylcarbamoyl)-cyclopent-1-enecarboxylic acid; 2-(4-Thiophen-3-yl-phenylcarbamoyl)-cyclopent-1-enecarboxylic acid; 2-(3-Fluoro-4'-methylsulfanyl-biphenyl-4-ylcarbamoyl)-cyclopent-1-enecarboxylic acid; 2-(2-Fluoro-4-thiophen-3-yl-phenylcarbamoyl)-cyclopent-1-enecarboxylic acid; 2-[4-(5-Chloro-thio-phen-2-yl-2-fluoro-phenylcarbomoyl]-cyclopent-1-enecarboxylic acid; 2-(4-Benzofuran-2-yl-2-fluoro-phenylcarbomoyl)-cyclopent-1-enecarboxylic acid; 2-(4-Benzo[b]thiophen-2-yl-2-fluoro-phenylcarbamoyl)-cyclopent-1-enecarboxylic acid; 2-[4-(2,4-Difluoro-benzysulfamoyl)-phenylcarbamoyl]-cyclopent-1-enecarboxylic acid; 2-(2'-Ethoxy-3-fluoro-biphenyl-4-ylcarbamoyl)-cyclopent-1-enecarboxylic acid; 2-(3-Fluoro-2'-methoxy-biphenyl-4-ylcarbamoyl)-cyclopent-1-enecarboxylic acid; 2-(3'-Ethoxy-3-fluoro-biphenyl-4-ylcarbamoyl)-cyclopent-1-enecarboxylic acid; 2-(3-Fluoro-3',4'-di-methoxy-biphenyl-4-ylcarbamoyl)-cyclopent-1-enecarboxylic acid; 2-(3-Fluoro-2',4'-di-methoxy-biphenyl-4-ylcarbamoyl)-cyclopent-1-enecarboxylic acid; 2-(3-Fluoro-4'-phenoxy-biphenyl-4-ylcarbamoyl)-cyclopent-1-enecarboxylic acid; 2-(3'-Acetyl-3-fluoro-biphenyl-4-ylcarbamoyl)-cyclopent-1-enecarboxylic acid; 2-(3-Fluoro-3'-trifluoromethoxy-biphenyl-4-ylcarbamoyl)-cyclopent-1-enecarboxylic acid; 2-(3-Fluoro-4'-trifluoromethoxy-biphenyl-4-ylcarbamoyl)-cyclopent-1-enecarboxylic acid; 4-[(2-Carboxy-cyclopent-1-enecarbonyl)-amino]-4'-phenoxy-biphenyl-3-carboxylic acid methyl ester; 4-(Biphenyl-4-ylcarbamoyl)-2,5-dihydro-thiophene-3-carboxylic acid; 2-(3'-Cyano-3-fluoro-biphenyl-4-ylcarbamoyl)-cyclopent-1-enecarboxylic acid; 2-(3-Fluoro-4'-methoxy-biphenyl-4-ylcarbamoyl)-cyclopent-1-enecarboxylic acid; 2-(3-Chloro-4'-methoxy-biphenyl-4-ylcarbamoyl)-cyclopent-1-enecarboxylic acid; 2-[2-Chloro-4-(6-methoxy-pyridin-3-yl)-phenylcarbamoyl]-cyclopent-1-enecarboxylic acid; 2-(2-Chloro-3'-cyano-byphenyl-4-ylcarbamoyl)-cyclopent-1-enecarboxylic acid; 2-(2-Chloro-4'-phenoxy-biphenyl-4-ylcarbamoyl)-cyclopent-1-enecarboxylic acid; 2-(3-Chloro-4'-phenoxy-biphenyl-4-ylcarbamoyl)-cyclopent-1-enecarboxylic acid; 2-[4-(2-Chloro-6-fluoro-benzyloxy)-phenylcarbamoyl]-cyclopent-1-enecarboxylic acid; 2-[4-(6-Methoxy-pyridin-3-yl)-2-trifluoromethyl-phenylcarbamoyl]-cyclopent-1-enecarboxylic acid; 2-(4'-Methoxy-3-trifluoromethyl-biphenyl-4-ylcarbamoyl)-cyclopent-1-enecarboxylic acid; 2-(3-Chloro-3'-cyano-biphenyl-4-ylcarbamoyl)-cyclopent-1-enecarboxylic acid; 2-[2-Fluoro-4-(6-methoxy-pyridin-3-yl)-phenylcarbamoyl]-cyclopent-1-enecarboxylic acid; 2-(2-Chloro-4'-methoxy-biphenyl-4-ylcarbamoyl)-cyclopent-1-ene-carboxylic acid; 2-(2-Chloro-4'-methanesulfonyl-biphenyl-4-ylcarbamoyl)-cyclopent-1-enecarboxylic acid; 2-(2-Chloro-4'-cyano-biphenyl-4-ylcarbamoyl)-cyclopent-1-ene-carboxylic acid; 2-(3-Chloro-4'-cyano-biphenyl-4-ylcarbamoyl)-cyclopent-1-enecarboxylic acid; 2-(4'-Cyano-3-fluoro-biphenyl-4-ylcarbamoyl)-cyclopent-1-enecarboxylic acid; 2-[3-Chloro-4-(6-methoxy-pyridin-3-yl)-phenylcarbamoyl]cyclopent-1-enecarboxylic acid; 2-(3'-Cyano-3-trifluoromethyl-biphenyl-4-ylcarbamoyl)-cyclopent-1-enecarboxylic acid; 2-(4'-Methanesulfonyl-3-triluoromethyl-biphenyl-4-ylcarbamoyl)-cyclopent-1-enecarboxylic acid; 2-(4'-Phenoxy-3-trifluoromethyl-biphenyl-4-ylcarbamoyl)-cyclopent-1-enecarboxylic acid; 2-(3'-Cyano-biphenyl-4-ylcarbamoyl)-cyclopent-1-enecarboxylic acid; 2-(4'-Cyano-biphenyl-4-ylcarbamoyl)-cyclopent-1-enecarboxylic acid; 2-(4'-Methoxy-biphenyl-4-ylcarbamoyl)-cyclopent-1-enecarboxylic acid; 2-(4'-Methoxy-2-methyl-biphenyl-4-ylcarbamoyl)-cyclopent-1-enecarboxylic acid; 2-(2-Methyl-4'-phenoxy-biphenyl-4-ylcarbamoyl)-cyclopent-1-enecarboxylic acid; 2-(4'-Cyano-2-methyl-biphenyl-4-ylcarbamoyl)-cyclopent-1-enecarboxylic acid; 2-[3,5-Dibromo-4-(2,5-difluoro-benzyloxy)-phenylcarbamoyl]-cyclopent-1-enecarboxylic acid; 2-[4-(3,4-Difluoro-benzyloxy)-phenylcarbamoyl]-cyclopent-1-enecarboxylic acid; 2-[4-(2,5-Difluoro-benzyloxy)-phenylcarbamoyl]-cyclopent-1-enecarboxylic acid; 2-[3,5-Dibromo-4-(3,4-difluoro-benzyloxy)-phenylcarbamoyl]-cyclopent-1-enecarboxylic acid; 2-[3,5-Dibromo-4-(2-chloro-6-fluoro-benzyloxy)-phenylcarbamoyl]-cyclopent-1-ene-carboxylic acid; 2-(3-Fluoro-3'-methoxy-biphenyl-4-ylcarbamoyl)-cyclopent-1-ene-carboxylic acid; 2-(3,3'-Difluoro-biphenyl-4-ylcarbamoyl)-cyclopent-1-enecarboxylic acid; 2-(4-Pyridin-3-yl-phenylcarbamoyl)-cyclopent-1-enecarboxylic acid; 2-(3-Chloro-4'-methanesulfonyl-biphenyl-4-ylcarbamoyl)-cyclopent-1-enecarboxylic acid; 2-(4'-Methanesulfonyl-biphenyl-4-ylcarbamoyl)-cyclopent-1-enecarboxylic acid; 2-[4-(6-Methoxy-pyridin-3-yl)-3-methyl-phenylcarbamoyl]-cyclopent-1-enecarboxylic acid; 2-[2-Cyano-4-(6-methoxy-pyridin-3-yl)-phenylcarbamoyl]-cyclopent-1-enecarboxylic acid; 2-(3-Chloro-4-pyridin-3-yl-phenylcarbamoyl)-cyclopent-1-enecarboxylic acid; 2-(2-Fluoro-4-pyridin-3-yl-phenylcarbamoyl)-cyclopent-1-enecarboxylic acid; 2-(3-Fluoro-4'-methanesulfonyl-biphenyl-4-ylcarbamoyl)-cyclopent-1-enecarboxylic acid; 2-[4-(6-Methoxy-pyridin-3-yl)-phenylcarbamoyl]-cyclopent-1-enecarboxylic acid; 2-(4'-Methanesulfonyl-2-methyl-biphenyl-4-ylcarbamoyl)-cyclopent-1-enecarboxylic acid; 4-[(2-Carboxy-cyclopent-1-enecarbonyl)-amino]-biphenyl-3-carboxylic acid methyl ester; 4-(4-Benzyloxy-3,5-dibromo-phenylcarbamoyl)-2,5-dihydro-thiophene-3-carboxylic acid; 4-(2'-Chloro-biphenyl-4-ylcarbamoyl)-2,5-dihydro-thiophene-3-carboxylic acid; 2-[(Biphenyl-2-ylmethyl)-carbamoyl]-cyclopent-1-enecarboxylic acid; 2-(4-Phenoxy-benzylcarbamoyl)-cyclopent-1-enecarboxylic acid; 2-[(Biphenyl-4-ylmethyl)-carbamoyl]-cyclopent-1-enecarboxylic acid; 2-[4'-(2-Carboxycyclopent-1-enecarbonylamino)-3,3'-di-methoxybiphenyl-4-ylcarbamoyl]cyclopent-1-enecarboxylic acid; 4-(3,5-Difluoro-3'-methoxy-biphenyl-4-ylcarbamoyl)-2,5-dihydro-furan-3-carboxylic acid; 4-[3,5-Dibromo-4-(2-chloro-6-fluoro-benzyloxy)-phenylcarbamoyl]-2,5-hydro-thio-phene-3-carboxylic acid; Cyclopent-1-ene-1,2-dicarboxylic acid mono-biphenyl-4-yl ester; 2-(4-Benzyloxy-3-chloro-phenylcarbamoyl)-cyclopent-1-enecarboxylic acid; 2-[3-Chloro-4-(2-chloro-6-fluoro-benzyloxy)-phenylcarbamoyl]-cyclopent-1-enecarboxylic acid; 2-[3-Chloro-4-(2-fluoro-benzyloxy)-phenylcarbamoyl]1-enecarboxylic acid; 2-(2-Phenyl-cyclopropylcarbamoyl)-cyclopent-1-enecarboxylic acid; 2-(4-Phenyl-butyl-carbamoyl)-cyclopent-1-enecarboxylic acid; 12-[3-Chloro-4-(2-trifluoromethyl-benzyl-oxy)-phenylcarbamoyl]-cyclopent-1-enecarboxylic acid; 2-(Biphenyl-4-yl-methyl-carbamoyl)-cyclopent-1-enecarboxylic acid; 2-(4'-Fluoro-3,3'-dimethyl-biphenyl-4-yl-carbomoyl)-cyclopent-1-enecarboxylic acid; 2-(3,5,4'-Trifluoro-3'-methyl-biphenyl-4-yl-carbamoyl)-cyclopent-1-enecarboxylic acid; 2-(3,5-Difluoro-2'-mehtoxy-biphenyl-4-yl-carbamoyl)-cyclopent-1-enecarboxylic acid; 2-(4-Bromo-2-methyl-phenylcarbamoyl)-cyclopent-1-enecarboxylic acid; 2-(3,2'-Dimethoxy-biphenyl-4-ylcarbamoyl)-cyclopent-1-enecarboxylic acid; 2-(3-Methoxy-biphenyl-4-ylcarbamoyl)-cyclopent-1-enecarboxylic acid; 2-(2'-Chloro-3-methoxy-biphenyl-4-ylcarbamoyl)-cyclopent-1-enecarboxylic acid; 2-(3-Methoxy-3'-trifluoromethoxy-biphenyl-4-ylcarbamoyl)-cyclopent-1-enecarboxylic acid; 2-(2'-Fluoro-3-methoxy-biphenyl-4-ylcarbamoyl)-cyclopent-1-enecarboxylic acid; 2-(3,2',4'-Trimethoxy-biphenyl- 4-ylcarbamoyl)-cyclopent-1-enecarboxylic acid; 2-(3'-Ethoxy-3-methoxy-biphenyl-4-ylcarbamoyl)-cyclopent-1-enecarboxylic acid; 2-(3,3'-Dimethoxy-biphenyl-4-ylcarbamoyl)-cyclopent-1-enecarboxylic acid; 2-(3-Fluoro-2'-methoxy-biphenyl-4-ylcarbamoyl)-cyclopent-1-enecarboxylic acid; 2-(3-Chloro-2'-methoxy-biphenyl-4-ylcarbamoyl)-cyclopent-1-enecarboxylic acid; 2-(2-Chloro-2'-methoxy-biphenyl-4-ylcarbamoyl)-cyclopent-1-enecarboxylic acid; 2-(2'-Methoxy-3-trifluoromethyl-biphenyl-4-ylcarbamoyl)-cyclopent-1-enecarboxylic acid; 2-(2,3,5,6-Tetrafluoro-2'-methoxy-biphenyl-4-ylcarbamoyl)-cyclopent-1-enecarboxylic acid; 2-(2'-Methoxy-3-methyl-biphenyl-4-ylcarbamoyl)-cyclopent-1-enecarboxylic acid; 2-(3,5-Dichloro-2'-methoxy-biphenyl-4-ylcarbamoyl)-cyclopent-1-enecarboxylic acid; 2-[2-(2-Methoxy-phenoxy)-5-trifluoromethyl-phenylcarbamoyl]-cyclopent-1-ene-carboxylic acid; 2-[2-(4-Chloro-3,5-dimethyl-phenoxy)-5-trifluoromethyl-phenyl-carbamoyl]-cyclopent-1-enecarboxylic acid; 2-[2-(4-Methoxy-phenoxy)-5-trifluoromethyl-phenylcarbamoyl]-cyclopent-1-enecarboxylic acid; 2-[2-(2,4-Dichloro-phenoxy)-phenyl-carbamoyl]-cyclopent-1-enecarboxylic acid; 2-[4-(2,4-Difluoro-phenoxy)-phenyl-carbamoyl]-cyclopent-1-enecarboxylic acid; 2-[4-(4-Chloro-phenoxy)-phenylcarbamoyl]-cyclopent-1-enecarboxylic acid; 2-(2'-Ethoxy-3,5-difluoro-biphenyl-4-ylcarbamoyl)-cyclopent-1-enecarboxylic acid; 2-(3'-Ethoxy-3,5-difluoro-biphenyl-4ylcarbamoyl)-cyclopent-1-enecarboxylic acid; 2-(3,5-Difluoro-3'-trifluoromethoxy-biphenyl-4-ylcarbamoyl)-cyclopent-1-enecarboxylic acid; 2-(3,5,2'-Trifluoro-biphenyl-4-yl-carbamoyl)-cyclopent-1-enecarboxylic acid; 2-(3,5-Difluoro-2',4'-dimethoxy-biphenyl-4-ylcarbamoyl)-cyclopent-1-enecarboxylic acid; 2-(2'-Methoxy-3-nitro-biphenyl-4-yl-carbamoyl)-cyclopent-1-enecarboxylic acid; 2-(3,5-Difluoro-2'-methoxy-biphenyl-4-yl-carbamoyl)-cyclopent-1-enecarboxylic acid.

The compounds of the formula (I) or of the formula (Ia) to be used according to the invention can form salts with inorganic or organic acids or bases. Examples of such salts are, for example, alkali metal salts, in particular sodium and potassium salts, or ammonium salts.

The compounds of formula (I) or of formula (Ia) may be obtained via various methods, including the method described in JP-A-50-121428. In preferred embodiments of the methods of the invention the two following methods of synthesis are used.

Method 1: In a first step the cycloalkene-1,2-dicarboxic acids can be obtained from the corresponding α,α'-dibromo alkanedicarboxylic acids as described by R. N. Mc Donald and R. R. Reitz, J. Org. Chem. 37, (1972) 2418-2422. Cyclopentene-1,2-dicarboxylic acid can also be obtained in large amounts from pimelic acid [D. C. Owsley und J. J. Bloomfield, Org. Prep. Proc. Int. 3, (1971) 61-70; R. Willstätter, J. Chem. Soc. (1926), 655-663].

Dicarboxylic acids substituted in or on the ring system can be synthesized in general via the cyanhydrine synthesis [Shwu-Jiüan Lee et. al., Bull. Inst. Chem. Academia Sinica Number 40, (1993), 1-10 or B. R. Baker at al., J. Org. Chem. 13, 1948, 123-133; and B. R. Baker at al., J. Org. Chem. 12, 1947, 328-332; L. A. Paquette et. al., J. Am. Chem. Soc. 97, (1975), 6124-6134].

The dicarboxylic acids can then be converted into the corresponding acid anhydrides by reacting them with acetic acid anhydride [P. Singh and S. M. Weinreb, Tetrahedron 32, (1976), 2379-2380].

Other methods for preparing different acid anhydrides of formula (II) are described in V. A. Montero at al., J. Org. Chem. 54, (1989), 3664-3667; P. ten Haken, J. Heterocycl. Chem. 7, (1970), 1211-1213; K. Alder, H. Holzrichter, J. Lieb. Annalen d. Chem. 524, (1936), 145-180; K. Alder, E. Windemuth, J. Lieb. Annalen d. Chem. 543, (1940), 56-78; and W. Flaig, J. Lieb. Annalen d. Chem. 568, (1950), 1-33.

These anhydrides may then be reacted with the corresponding amines to the desired amides of formula (I) or of formula (Ia). This reaction can be carried out either by use of the reaction conditions as described in J. V. de Julian Ortiz et al., J. Med. Chem. 42, (1999), 3308 (designated route A in Example 1) or by use of 4-dimethylamino pyridine (designated route B in Example 1).

Method 2: The amides of formula (I) or of formula (Ia) can also be synthesized by reacting an amine of the formula (IV) with an arylboronic-acid of the general formula (V) [M. P. Winters, Tetrahedron Lett., 39, (1998), 2933-2936].

Biarylaniline can be synthesized in general via the palladium coupling [G. W. Kabalka et al., Chem. Commun., (2001), 775; A. Demeter, Tetrahedron Lett. 38; (1997), 5219-5222; V. Snieckus, Chem. Commun. 22, (1999), 2259-2260].

Method 3: The amides of formula (I) or of formula (Ia) can also be synthesized by reacting an halogen derivative of the formula (VI) with an arylboronic acid of the general formula (VII) or formula (VIIa) [N. E. Leadbeater, S. M. Resouly, Tetrahedron, 55, 1999, 11889-11894].

Method 4: The compounds of formula (I) [r=0] or of formula (Ia) [r=0] can be synthesized by reacting an amine of the formula (III) with a compound of the formula (VIII) [Bew, J. Chem. Soc. 1955, 1775-1777].

The compounds of the present invention can be used for a variety of human and animal diseases, preferably human diseases, where inhibition of the pyrimidine metabolism is beneficial. Such diseases are:

fibrosis, uveitis, rhinitis, asthma or athropathy, in particular, arthrosis all forms of rheumatism acute immunological events and disorders such as sepsis, septic shock, endotoxic shock, Gram-negative sepsis, toxic shock sydrome, acute respiratory distress syndrome, stroke, reperfusion injury, CNS injury, serious forms of allergy, graft versus host and host versus graft reactions, alzheimer's or pyresis, restenosis, chronic pulmonary inflammatory disease, silicosis, pulmonary sarcosis, bone resorption disease. These immunological events also include a desired modulation and suppression of the immune system;

all types of autoimmune diseases, in particular rheumatoid arthritis, rheumatoid spondylitis, osteoarthritis, gouty arthritis, multiple sclerosis, insulin dependent diabetes mellitus and non-insulin dependent diabetes, and lupus erythematoidis, ulcerative colitis, Morbus Crohn, inflammatory bowel disease, as well as other chronic inflammations, chronic diarrhea;

dermatological disorders such as psoriasis progressive retinal atrophy all kinds of infections including opportunistic infections.

The compounds according to the invention and medicaments prepared therewith are generally useful for the treatment of cell proliferation disorders, for the treatment or prophylaxis, immunological diseases and conditions (as for instance inflammatory diseases, neuroimmunological diseases, autoimmune diseases or other).

The compounds of the present invention are also useful for the development of immunomodulatory and anti-inflammatory medicaments or, more generally, for the treatment of diseases where the inhibition of the pyrimidine biosynthesis is beneficial.

The compounds of the present invention are also useful for the treatment of diseases which are caused by malignant cell proliferation, such as all forms of hematological and solid cancer. Therefore the compounds according to the invention and medicaments prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

These diseases and conditions include but are not limited to cancer such as hematological (e.g. leukemia, lymphoma, myeloma) or solid tumors (for example breast, prostate, liver, bladder, lung, esophageal, stomach, colorectal, genitourinary, gastrointestinal, skin, pancreatic, brain, uterine, colon, head and neck, and ovarian, melanoma, astrocytoma, small cell lung cancer, glioma, basal and squameous cell carcinoma, and sarcomas such as Kaposi's sarcoma and osteosarcoma), treatment of disorders involving T-cells such as aplastic anemia and DiGeorge syndrome, and Graves' disease.

Leflunomide, was previously found to inhibit HCMV replication in cell culture. Ocular herpes is the most common cause of infectious blindness in the developed world. There are about 50,000 cases per year in the US alone, of which 90% are recurences of initial infections. Recurrences are treated with antivirals and corticosteroids. Cytomegalovirus another herpes virus is a common cause of retinal damage and blindness in patients with aids. The compounds of the present invention can be used alone or in combination with other antiviral compounds such as Ganciclovir and Foscarnet to treat such diseases.

The compounds of the present invention can further be used for diseases that are caused by protozoal infestations in humans and animals. Such veterinary and human pathogenic protozoas are preferably intracellular active parasites of the phylum Apicomplexa or Sarcomastigophora, especially Trypanosoma, Plasmodia, Leishmania, Babesia and Theileria, Cryptosporidia, Sacrocystida, Amoebia, Coccidia and Trichomonadia. These active substances or corresponding drugs are especially suitable for the treatment of Malaria tropica, caused by *Plasmodium falciparum*, Malaria tertiana, caused by *Plasmodium vivax* or *Plasmodium ovale* and for the treatment of Malaria quartana, caused by *Plasmodium malariae*. They are also suitable for the treatment of Toxoplasmosis, caused by *Toxoplasma gondii*, Coccidiosis, caused for instance by *Isospora belli*, intestinal Sarcosporidiosis, caused by *Sarcocystis suihominis*, dysentery caused by *Entamoeba histolytica*, Cryptosporidiosis, caused by *Cryptosporidium parvum*, Chargas disease, caused by *Trypanosoma cruzi*, sleeping sickness, caused by *Trypanosoma brucei rhodesiense* or *gambiense*, the cutaneous and visceral as well as other forms of Leishmaniosis. They are also suitable for the treatment of animals infected by veterinary pathogenic protozoa, like *Theileria parva*, the pathogen causing bovine East coast fever, *Trypanosoma congolense congolense* or *Trypanosoma vivax, Trypanosoma brucei brucei*, pathogens causing Nagana cattle disease in Africa, *Trypanosoma brucei evansi* causing Surra, *Babesia bigemina*, the pathogen causing Texas fever in cattle and buffalos, *Babesia bovis*, the pathogen causing european bovine Babesiosis as well as Babesiosis in dogs, cats and sheep, *Sarcocystis ovicanis* and *ovifelis* pathogens causing Sarcocystiosis in sheep, cattle and pigs, Cryptosporidia, pathogens causing Cryptosporidioses in cattle and birds, Eimeria and Isospora species, pathogens causing Coccidiosis in rabbits, cattle, sheep, goats, pigs and birds, especially in chickens and turkeys. The use of the compounds of the present invention is preferred in particular for the treatment of Coccidiosis or Malaria infections, or for the preparation of a drug or feed stuff for the treatment of these diseases. This treatment can be prophylactic or curative. In the treatment of malaria, the compounds of the present invention may be combined with other anti-malaria agents.

The compounds of the present invention can further be used for viral infections or other infections caused for instance by *Pneumocystis carinii*.

The compounds of the formula (I) or of the formula (Ia) and their pharmacologically acceptable salts can be administered to animals, preferably to mammals, and in particular to humans, dogs and chickens as therapeutics per se, as mixtures with one another or in the form of pharmaceutical preparations which allow enteral or parenteral use and which as active constituent contain an effective dose of at least one compound of the formula (I) or of the formula (Ia) or a salt thereof, in addition to customary pharmaceutically innocuous excipients and additives. The compounds of formula (I) or of the formula (Ia) can also be administered in form of their salts, which are obtainable by reacting the respective compounds with physiologically acceptable acids and bases.

The therapeutics can be administered orally, e.g. in the form of pills, tablets, coated tablets, sugar coated tablets, hard and soft gelatin capsules, solutions, syrups, emulsions or suspensions or as aerosol mixtures. Administration, however, can also be carried out rectally, e.g. in the form of suppositories, or parenterally, e.g. in the form of injections or infusions, or percutaneously, e.g. in the form of ointments, creams or tinctures.

In addition to the active compounds of formula (I) or of formula (Ia), the pharmaceutical composition can contain further customary, usually inert carrier materials or excipients. Thus, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants. They can also contain two or more compounds of the formula (I) or of the formula (Ia) or their pharmacologically acceptable salts and also other therapeutically active substances.

Thus, the compounds of the present invention can be used in the form of one substance alone or in combination with other active compounds—for example with medicaments already known for the treatment of the aforementioned diseases, whereby in the latter case a favorable additive, amplifying effect is noticed. Suitable amounts to be administered to humans range from 5 to 500 mg.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight preferably 1 to 50 mg/kg. Suitable dosage rates for larger mammals, for example humans, are of the order of from about 10 mg to 3 g/day, conveniently administered once, in divided doses 2 to 4 times a day, or in sustained release form.

In general, a daily dose of approximately 10 mg to 5000 mg, preferably 50 to 500 mg, per human individual is appropriate in the case of the oral administration which is the preferred form of administration according to the invention. In the case of other administration forms too, the daily dose is in similar ranges.

The compounds of formula (I) or of formula (Ia) can also be used in the form of a precursor (prodrug) or a suitably modified form, that releases the active compound in vivo. Such precursors such as the preferred embodiments of $R^6$ can be obtained for example by masking the free acid group with an ester group, which is then in turn transformed into the free acid group in vivo [F. W. Sum et. al. Bioorg. & Med. Chem. Lett. 9 (1999), 1921-1926; Ada Rephaeli et. al. Drug Development Research 50 (2000) 379-391; H. Ishikawa, Current Med. Chem. 6 (1999), 575-597]. Also such precursors for the preferred embodiments of $R^5$ can be obtained for example by masking the amidine with an hydroxy group, which is then in turn transformed into the free amidine in vivo [R. M. Scarborough, J. Med. Chem. 43, 19, (2000), 3454-3473].

The invention is further illustrated by the following non-limiting Examples and Table 1, which show examples for the synthesis of the compounds of the present invention and demonstrate their DHODH inhibiting effect.

EXAMPLES

1. Synthesis of Compounds of Formula (I)

The compounds of formula (I) were obtained through synthesis route (A) or (B). The amines were purchased from Sigma-Aldrich Chemie GmbH, Günwalder Weg 30, D-82041 Deisenhofen, Maybridge, plc Trevillet, Tintangel, Cornwall PL34 OHW, England or synthesized by a general procedure for biarylanilines.

Synthesis of 4-aminophenylbenzyl ether

A mixture of p-nitrophenole (5 mmol), NaOH (7.5 mmol), water (10 ml), i-propanol (10 ml), $CH_2Cl_2$ (15 ml), $Et_3N^+CH_2Ph^*Cl^-$ (1.4 mmol) and benzylchloride (5.8 mmol) was stirred for 2 days. The lower layer was separated, washed with a solution of $Na_2CO_3$, then with water, and evaporated to dryness to yield 60%. A mixture of Fe-powder (1.3 g), water (3 ml), AcOH (0.25 ml), $NH_4Cl$ (0.08 g), ethanol (5 ml) and the nitro compound (5.2 mmol) was refluxed under stirring at 60-70° C. for 2 hours. The precipitate of iron oxide was filtered and washed with 30 ml ethanol. The combined liquids were evaporated to dryness. The residue was diluted with water, filtered off, washed with water, dried at <70° C. and reprecipitated from $CCl_4$ with hexane. Yields 50%.

General Procedure for the Synthesis of Biarylanilines:

General Procedure I:

Aryl bromide (100 mg, 1 eq), aryl- or heteroaryl- boronic acid (1.2 eq, 0.6 nmuol), $PFd(PPh_3)_4$ (0.03 eq), and caesium carbonate (1.5 eq) were dissolved in a mixture of 1,2-dimethoxyethane (3 ml) and water (1 ml). The mixture was stirred for 16 h under reflux. The mixture was then allowed to cool to room temperature. After separation of the aqueous and the organic phase, the aqueous phase was washed with EtOAc and the combined organic phases were concentrated, and then purified by preparative thin layer chromatography (Merck, 20×20 cm, Silica gel 60 $F_{254}$, 1 mm) using (n-hexane:EtOAc, 8:2) as an eluent.

General Procedure II:

Arylboronic acid (2.5 eq), palladium black (0.25 eq), potassium fluoride (6.5 eq) and 4-iodoaniline (1 eq) were triturated in n-butanol (1 eq) and stirred for 8 hours under reflux. The reaction mixture was filtered, the solvent removed in vacuo and the residue purified by silicagel chromatography using hexane:EtOAc (7:3) as an eluent.

General Procedure for the Synthesis of Compounds of Formula (I)

Synthesis Route (A):

A solution of the corresponding amine (1 eq) was added slowly to a solution of the dicarboxylic acid (1 eq) in toluene at 60° C. The mixture was stirred at this temperature for 1 hour, then allowed to cool to room temperature and filtered. The precipitate was washed with 2 M HCl and then recrystallized from ethanol:water (1:1). The amide thus obtained was characterized by HPLC-mass spectroscopy.

Synthesis Route (B):

A solution of the corresponding amine (1 eq) in dry dichloromethane was added slowly to a solution of the dicarboxylic acid anhydride (1 eq) and 4-dimethylamino pyridine (1 eq) in dry dichloromethane at ambient temperature. After 16 hours, the mixture was concentrated by evaporation in vacuo. The residue was taken up in ethyl acetate and the organic phase was washed with water, dried over sodium sulfate, filtered and concentrated in vacuo. The residue opatined was the corresponding amide which was characterized by HPLC-mass spectroscopy.

Synthesis Route (C):

A solution of the corresponding amine (1 eq) in dry dichloromethane was added slowly to a solution of the dicarboxylic acid anhydride (1 eq) in dry dichloromethane at ambient temperature. After 16 hours, the mixture was concentrated in vacuo. The residue opatined was taken up in ethyl acetate and the organic phase was washed with water, dried over sodium sulfate, filtered and concentrated in vacuo. The residue opatined was the corresponding amide which was characterized by HPLC-mass spectroscopy.

Compounds 1 and 2 were synthesized as described in method A and B. Compounds 13 to 52 were synthesized according to method C. All other compounds were synthesized as described in method B.

EXAMPLES (Compound 1) (Synthesis Route A)

A solution of 117 mg (0.5 mmol) 4-benzyloxyphenylamine-hydrochloride in 1 ml of toluene was added slowly to a solution of 69 mg (0.5 mmol) 5,6-dihydro-4H-cyclopenta[c]furan-1,3-dione in 2 ml of toluene at 60° C. The mixture was stirred at this temperature for 1 hour, then cooled to room temperature and filtrated. The precipitate was washed with 2 M HCl and then recrystallized from ethanol/water (1:1) yielding 158 mg (85%) of the product.

(Compound 2) (Synthesis Route A)

A solution of 8.6 g (51 mmol) biphenyl-4-amine in 50 ml of toluene was added slowly to a solution of 7.0 g (51 mmol) 5,6-dihydro-4H-cyclopenta[c]furan-1,3-dione in 50 ml of toluene at 60° C. The mixture was stirred at this temperature for 1 hour, then cooled to room temperature and filtrated. The precipitate was washed with 2 M HCl and then recrystallized from ethanol:water (1:1) yielding 14 g (91%) of the product.

(Compound 47) (Synthesis Route C)

2,5-Dihydrofitran-3,4-dicarboxylic acid (1 eq) was solved in dry dichlormethylen and acetic anhydride (10 eq) was added. The mixture was stirred for 15 hours at room temperature. The solvent was removed in vacuo. The aniline (1 eq) was added to the solid product and solved in dry dichloromethylene. The mixture was stirred for 15 hours at room temperature. The solvent was removed in vacuo and the product was crystallized from ethanol:water (1:1). Yield 75-90%.

(Compound 49) (Synthesis Route C)

4-(Biphenyl-4-ylcarbamoyl)-2,5-dihydro thiophene-3-carboxylic acid (1 eq) was synthesized by Synthesis Route C and 3-chloroperoxybenzoic acid (10 eq) were solved in dichloromethylen. The mixture was stirred for 5 hours at room temperature. After separating the solvent, the product was crystallized from ethanol/water 1:1. Yield: 51%.

Synthesis of 2,5-dihydro thiophene-3,4-dicarboxylic anhydride

To a solution of 4-oxotetrahydro thiophene-3-carboxylic acid methyl ester (4 g, 25 mmol) in methanol (7 ml), cooled at 0° C., a solution of potassium cyanide (1.68 g, 30 mmol) in water (10 ml) was added. The mixture was acidified with acetic acid (1.5 ml, 25 mmol) and stirred at 0° C. for 8 hours. Then the mixture was acidified with $H_3PO_4$ and diluted with brine (50 ml) and extracted with $CH_2Cl_2$ (4×30 ml). The organic layers were dried over sodium sulfate and concentrated to give 4-cyano-tetrahydro thiophene-3-carboxylic acid methyl ester in 75% yield.

4-Cyano-tetrahydro thiophene-3-carboxylic acid methyl ester (3.5 g, 18.7 mmol) was refluxed in a mixture of acetic acid (10 ml) and concentrated HCl (15 ml) for 20 hours. The solution was diluted with water (50 ml) and then clarified with active carbon. The reaction mixture was filtered and concentrated under reduced pressure. The residue was dissolved in water (30 ml) and concentrated again. The solid residue was triturated with acetone, filtered from ammonium chloride and concentrated in vacuo to give 3-hydroxy-tetrahydro thiophene 3,4-dicarboxylic acid 4-methyl ester in 80% yield.

A solution of 3-hydroxy tetrahydro thiophene-3,4-dicarboxylicacid-4-methylester (2.87 g, 14.9 mmol) in acetic anhydride (20 ml) was refluxed for 4 h. The reaction mixture was filtered and concentrated under reduce pressure. The solid residue was triturated with acetone, dried with $Na_2SO_4$ and concentrated in vacuo. The solid product was recrystallized from benzene to give 2,5-dihydrothiophene-3,4-dicarboxylic anhydride in 26% yield.

Synthesis of 2,5-dihydro furan 3,4-dicarboxylic acid 2.3 g (0.1 mol) sodium was pulverized under toluene and the solvent was replaced with 75 ml ether. 11 ml (0.1 mol) methylglycolate was added to the mixture under stirring until the evolution of hydrogen gas had ceased. To the dry sodium derivative remaining after destillation of the ether, a solution of 10 ml (0.12 mol) distilled methylacrylate in 50 ml DMSO was added while the reaction was kept at 4° C. After 15 minutes the solution was stirred for an additional 30-40 min at room temperature. and poured into aqueous $H_2SO_4$ at 4° C. and extracted with ether. Washing of the organic layer with a saturated NaCl solution, drying over $NaSO_4$ and removal of the ether was followed by destillation under reduced pressure to give 4.5 g (31%) of 4-oxo-tetrahydro furane 3-carboxylic acidmethyl ester.

To a stirred solution of 3.9 g (60 mmol) KCN in 5.5 ml of water at 4° C., a solution of 2.9 g (20 mmol) of 4-oxo-tetrahydro furane 3-carboxylic acid methyl ester in ether (26 ml) was added. To the precipitate of salts, 3.5 ml $H_2SO_4$ (18 N) was added and stirred for 16 hours. Then the organic solution was separated, the salts were washed twice with benzene, dried over sodium sulfate and concentrated in vacuo to give 4-cyano-tetrahydro furane 3-carboxylic acid methyl ester.

4-Cyano-tetrahydro furane 3-carboxylic acid methyl ester was dissolved in 4.9 ml of pyridine and treated with 4.4 ml (60 mmol) of $SOCl_2$ during 90 min under nitrogen at 4° C. The resulting solution was warmed to room temperature, stirred for 6 hours and poured into 40 ml water at 4° C. and extracted with benzene. Combined extracts were dried and concentrated in vacuo to give 90% yield of 4-cyano-2,5-dihydro furane 3-carboxylic acid methyl ester.

1.1 g of 4-cyano-2,5-dihydro furane 3-carboxylic acid methyl ester was refluxed for 3 hours in 6 ml of conc. HCl. The solution was allowed to stand overnight at 5° C. Then the precipitate (0.55 g) was filtered off and the water solution was evaporated in vacuo, and the residue was treated with EtOAc. The organic solution was dried and evaporated in vacuo to give 0.4 g of precipitate. Combined precipitates were purified on silica gel to give 2,5- dihydro furan-3,4-dicarboxylic acid (0,8 g)

1a. Synthesis of Compounds of Formula (Ia)

Compound 11 was synthesized as described in method B.

2. Inhibition Assay of DHODH Activity

The standard assay mixture contained 50 μM decyclo ubichinone, 100 μM dihydroorotate, 60 μM 2,6-dichloroindophenol, as well as 20 mU DHODH. The volume activity of the recombinant enzyme used was 30 U/ml. Measurements were conducted in 50 mM TrisHCl (150 mM KCl, 0,1% Triton X-100, pH. 8,0) at 30° C. in a final volume of 1 ml. The components were mixed, and the reaction was started by adding dihydroorotate. The course of reaction was followed by spectrophotometrically measuring the decrease in absorption at 600 nm for 2 min.

Inhibitory studies were conducted in a standard assay with additional variable amounts of inhibitor. For the determination of the $IC_{50}$ values (concentration of inhibitor required for 50% inhibition) at least five different inhibitor concentrations were applied.

These investigations were carried out with recombinant human as well as with recombinant murine DHODH provided by Prof. M. Löffler, Marburg, Germany [M. Löffler, Chem. Biol. Interact. 124, (2000), 61-76].

As a reference the active metabolite of leflunomide A77-1726 (Compound 12) was used [J. Jöckel et. al. Biochemical Pharmacology 56 (1998), 1053-1060].

The results of the inhibition assay are shown in the following Table 1. It is evident from the comparison of the $IC_{50}$-values that the compounds used in the present invention not only have a comparable or even better inhibitory activity on the human enzyme than the active metabolite of leflunomide but also a higher specifity for the human enzyme.

TABLE 1

| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 01 | 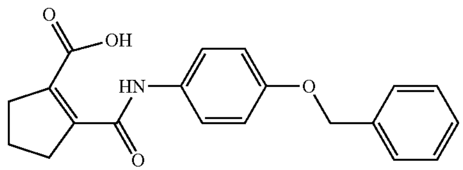 | N.D. | 337.37 | 338 [M + H]⁺ | 0.350 | 8.2 | N.D. |
| 02 | 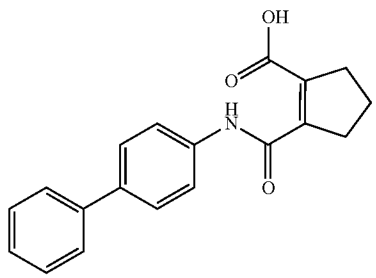 | δ=1.93 (m$_C$, 2H, CH$_2$), 2.66 (m$_C$, 2H, CH$_2$), 2.79 (m$_C$, 2H, CH$_2$), 7.33 (m, 1H, CH$_{ar}$), 7.45 (m, 1H, CH$_{ar}$), 7.64 (m, 1H, CH$_{ar}$), 7.72 (m$_C$, 2H, CH$_{ar}$), 10.34 (s, 1H, NH). | 307.35 | 306 [M − H]⁺ | 0.690 | 4.0 | N.D. |
| 03 | 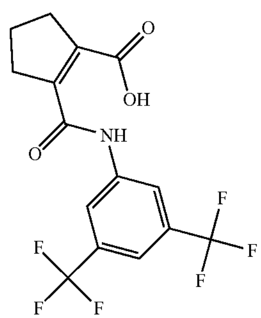 | N.D. | 367.24 | 366 [M − H]⁺ | 1.0 | N.D. | N.D. |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 04 | *structure* | N.D. | 352.39 | 353 [M + H]⁺ | 1.0 | weakly active | N.D. |
| 05 | *structure* | N.D. | 536.55 | 537 [M + H]⁺ | 1.1 | weakley active | N.D. |
| 06 | *structure* | N.D. | 303.21 | 302 [M − H]⁺ | 1.3 | N.D. | N.D. |

TABLE 1-continued

| N | Structure | ¹H-NMR | Molecule-Mass [g/mol] | HPLC/MS (ESI) | human IC$_{50}$-Value [µM] | murine IC$_{50}$-Value [µM] | rate IC$_{50}$-Value [µM] |
|---|---|---|---|---|---|---|---|
| 07 | *pentafluoro-trifluoromethyl phenyl cyclopentene carboxamide* | N.D. | 371.21 | 370 [M − H]⁺ | 1.6 | N.D. | N.D. |
| 08 | *4-(trifluoromethyl)phenyl cyclopentene carboxamide* | N.D. | 299.25 | 300 [M + H]⁺ | 1.6 | 0.93 | N.D. |
| 09 | *3-(trifluoromethyl)phenyl cyclopentene carboxamide* | N.D. | 299.25 | 300 [M + H]⁺ | 6.8 | 55 | N.D. |

TABLE 1-continued

| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 10 | (structure) | N.D. | 285.22 | 286 [M + H]⁺ | 6.8 | N.D. | N.D. |
| 11 | (structure) | N.D. | 352.38 | 353 [M + H]⁺ | 7.0 | N.D. | N.D. |
| 12 | (structure) | N.D. | 272.22 | | 0.670 | 0.20 | N.D. |
| 13 | (structure) | δ=1.91 (m$_C$, 2H, CH₂), 2.65 (m$_C$, 2H, CH₂), 2.78 (m$_C$, 2H, CH₂), 7.27-7.51 (m, 6H, CH$_{Ar}$), 7.72 (d, 2H, CH$_{Ar}$), 10.40 (s, 1H, NH), 12.67 (s, 1H, OH). | 325 | 326 [M + H]⁺ | A | C | C |

TABLE 1-continued

| N | Structure | $^1$H-NMR | Molecule-Mass [g/mol] | HPLC/MS (ESI) | human IC$_{50}$-Value [µM] | murine IC$_{50}$-Value [µM] | rate IC$_{50}$-Value [µM] |
|---|---|---|---|---|---|---|---|
| 14 | (2'-chloro-biphenyl with cyclopentene dicarboxamide) | δ=1.95 (m$_C$, 2H, CH$_2$), 2.65 (m$_C$, 2H, CH$_2$), 2.78 (m$_C$, 2H, CH$_2$), 7.35-7.72 (m, 8H, CH$_{Ar}$), 10.36 (s, 1H, NH), 12.66 (s, 1H, OH). | 341 | 342 [M + H]$^+$ | A | C | C |
| 15 | (2'-methoxy-biphenyl with cyclopentene dicarboxamide) | δ=1.94 (m$_C$, 2H, CH$_2$), 2.66 (m$_C$, 2H, CH$_2$), 2.79 (m$_C$, 2H, CH$_2$), 3.76 (s, 3H, O—CH$_3$), 7.01-7.67 (m, 8H, CH$_{Ar}$), 10.30 (s, 1H, NH). | 337 | 338 [M + H]$^+$ | A | N.D. | N.D. |
| 16 | (2,6-difluorobenzyloxy-phenyl with cyclopentene dicarboxamide) | δ=1.90 (m$_C$, 2H, CH$_2$), 2.57 (m$_C$, 2H, CH$_2$), 2.76 (m$_C$, 2H, CH$_2$), 5.08 (s, 2H, CH$_2$—O), 6.95-7.57 (m, 7H, CH$_{Ar}$), 10.11 (s, 1H, NH), 11.33 (s, 1H, OH). | 373 | 374 [M + H]$^+$ | A | N.D. | N.D. |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 17 | 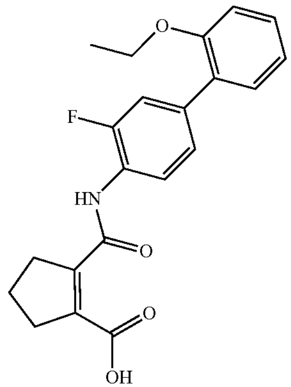 | δ=1.04 (m$_C$, 3H, O—CH$_2$—CH$_3$), 1.65 (m$_C$, 2H, CH$_2$), 2.45 (m$_C$, 2H, CH$_2$), 2.55 (m$_C$, 2H, CH$_2$), 3.82 (m$_C$, 2H, O—CH$_2$—CH$_3$), 6.75–6.87 (m, 2H, CH$_{Ar}$), 7.06-7.28 (m, 4H, CH$_{Ar}$), 7.71-7.77 (m, 1H, CH$_{Ar}$), 10.23 (s, 1H, NH), 12.83 (s, 1H, OH). | 369 | 370 [M + H]$^+$ | A | N.D. | N.D. |
| 18 | 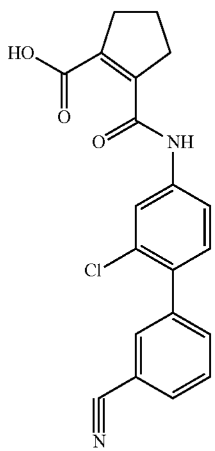 | δ=1.7 (m$_C$, 2H, CH$_2$), 2.60 (m$_C$, 2H, CH$_2$), 2.73 (m$_C$, 2H, CH$_2$), 7.36-7.91 (m, 7H, CH$_{Ar}$), 10.61 (s, 1H, NH), 12.61 (s, 1H, OH). | 366 | 367 [M + H]$^+$ | A | N.D. | N.D. |

TABLE 1-continued

| N | Structure | $^1$H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 19 | (4-methoxyphenyl biphenyl chloro cyclopentene carboxylic acid amide) | δ=2.16 (m$_C$, 2H, CH$_2$), 2.89 (m$_C$, 2H, CH$_2$), 3.01 (m$_C$, 2H, CH$_2$), 4.03 (s, 3H, O—CH$_3$), 7.23-8.15 (m, 7H, CH$_{Ar}$), 10.66 (s, 1H, NH), 13.00 (s, 1H, OH). | 371 | 372 [M + H]$^+$ | A | A | A |
| 20 | (4-methylsulfonyl biphenyl chloro cyclopentene carboxylic acid amide) | δ=2.7 (m$_C$, 2H, CH$_2$), 2.79 (m$_C$, 2H, CH$_2$), 2.90 (m$_C$, 2H, CH$_2$), 3.40 (s, 3H, SO$_2$—CH$_3$), 7.54-8.14 (m, 7H, CH$_{Ar}$), 10.65 (s, 1H, NH), 12.83 (s, 1H, OH). | 429 | 420 [M + H]$^+$ | B | N.D. | N.D. |
| 21 | (4-cyanobiphenyl chloro cyclopentene carboxylic acid amide) | δ=1.86 (m$_C$, 2H, CH$_2$), 2.59 (m$_C$, 2H, CH$_2$), 2.71 (m$_C$, 2H, CH$_2$), 7.33-7.90 (m, 7H, CH$_{Ar}$), 10.44 (s, 1H, NH), 12.62 (s, 1H, OH). | 366 | 367 [M + H]$^+$ | B | N.D. | N.D. |
| 22 | (6-methoxypyridyl phenyl chloro cyclopentene carboxylic acid amide) | δ=1.74 (m$_C$, 2H, CH$_2$), 2.48 (m$_C$, 2H, CH$_2$), 3.71 (s, 3H, O—CH$_3$), 6.70-8.02 (m, 6H, CH$_{Ar}$), 10.28 (s, 1H, NH), 12.48 (s, 1H, OH). | 372 | 373 [M + H]$^+$ | A | N.D. | N.D. |

TABLE 1-continued

| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 23 | (structure) | δ=1.92 (m_C, 2H, CH₂), 2.50 (s, 3H, CH₃), 2.66 (m_C, 2H, CH₂), 2.79 (m_C, 2H, CH₂), 3.79 (s, 3H, O—CH₃), 6.97-7.54 (m, 7H, CH_Ar), 10.20 (s, 1H, NH), 12.00 (s, 1H, OH). | 351 | 352 [M + H]⁺ | A | N.D. | N.D. |
| 24 | (structure) | δ=1.92 (m_C, 2H, CH₂), 2.64 (m_C, 2H, CH₂), 2.74 (m_C, 2H, CH₂), 5.02 (s, 2H, O—CH₂), 7.28-7.93 (m, 5H, CH_Ar), 10.41 (s, 1H, NH), 12.68 (s, 1H, OH). | 529 | 530 [M + H]⁺ | A | B | C |

TABLE 1-continued

| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 25 | 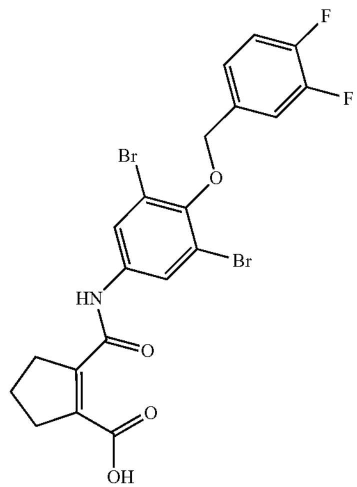 | δ=1.83 (m_C, 2H, CH₂), 2.55 (m_C, 2H, CH₂), 2.65 (m_C, 2H, CH₂), 4.86 (s, 2H, O—CH₂), 7.28-7.85 (m, 5H, CH_Ar), 10.34 (s, 1H, NH), 12.56 (s, 1H, OH). | 529 | 530 [M + H]⁺ | A | N.D. | N.D. |
| 26 | 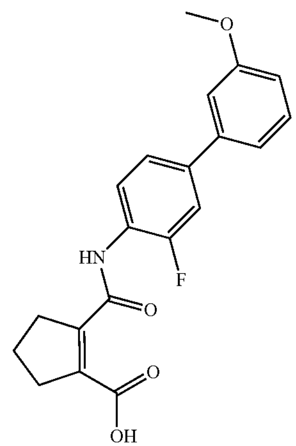 | δ=1.89 (m_C, 2H, CH₂), 2.69 (m_C, 2H, CH₂), 2.80 (m_C, 2H, CH₂), 3.83 (s, 3H, O—CH₃), 6.92-8.09 (m, 7H, CH_Ar), 10.57 (s, 1H, NH). | 355 | 356 [M + H]⁺ | A | C | C |

TABLE 1-continued
| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 27 | 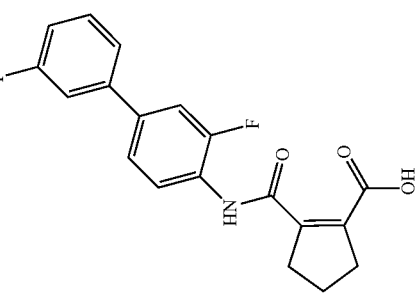 | δ=1.67 (m_C, 2H, CH₂), 2.47 (m_C, 2H, CH₂), 2.58 (m_C, 2H, CH₂), 6.94-7.91 (m, 7H, CH_Ar), 10.40 (s, 1H, NH), 12.81 (s, 1H, OH). | 343 | 344 [M + H]⁺ | A | C | N.D. |
| 28 | 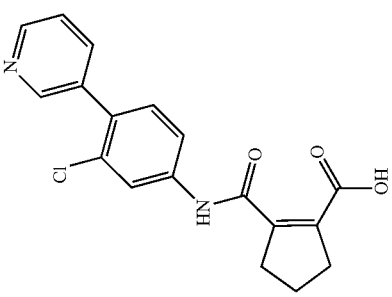 | δ=1.92 (m_C, 2H, CH₂), 2.66 (m_C, 2H, CH₂), 2.77 (m_C, 2H, CH₂), 7.41-8.62 (m, 7H, CH_Ar), 10.62 (s, 1H, NH), 12.68 (s, 1H, OH). | 342 | 343 [M + H]⁺ | B | N.D. | N.D. |

TABLE 1-continued

| N | Structure | $^1$H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 29 | (structure with dibromo-benzyloxyphenyl and thiophene-carboxylic acid) | δ=3.93 (m$_C$, 2H, CH$_2$), 4.03 (m$_C$, 2H, CH$_2$), 4.87 (s, 2H, O—CH$_2$), 7.30-7.83 (m, 7H, CH$_{Ar}$), 10.49 (s, 1H, OH). | 511 | 512 [M + H]$^+$ | A | C | B |
| 30 | (structure with 4-fluoro-3-methylphenyl biphenyl cyclopentene carboxylic acid) | δ(CD$_3$OD)=1.91 (m$_C$, 2H, CH$_2$), 2.32 (s, 3H, CH$_3$), 2.84 (m$_C$, 2H, CH$_2$), 2.93 (m$_C$, 2H, CH$_2$), 7.11 (m$_C$, 1H, CH$_{Ar}$), 7.29 (s, 1H, CH$_{Ar}$), 7.32 (s, 1H, CH$_{Ar}$), 7.43- 7.56 (m, 2H, CH$_{Ar}$). | 375 | 376 [M + H]$^+$ | A | N.D. | N.D. |
| 31 | (structure with 2-methoxyphenyl biphenyl difluoro cyclopentene carboxylic acid) | δ(CD$_3$OD)=2.00 (m$_C$, 2H, CH$_2$), 2.84 (m$_C$, 2H, CH$_2$), 2.94 (m$_C$, 2H, CH$_2$), 3.83 (s, 3H, O—CH$_3$), 7.00-7.10 (m, 2H, CH$_{Ar}$), 7.18 (s, 1H, CH$_{Ar}$), 7.21 (s, 1H, CH$_{Ar}$), 7.31-7.39 (m, 2H, CH$_{Ar}$). | 373 | 374 [M + H]$^+$ | A | N.D. | N.D. |
| 32 | (structure with 2-methoxyphenyl, nitro biphenyl cyclopentene carboxylic acid) | δ=1.90 (m$_C$, 2H, CH$_2$), 2.64 (m$_C$, 2H, CH$_2$), 2.74 (m$_C$, 2H, CH$_2$), 3.76 (s, 3H, O—CH$_3$), 7.03 (m$_C$, 1H, CH$_{Ar}$), 7.11 (m$_C$, 1H, CH$_{Ar}$), 7.34 (s, 1H, CH$_{Ar}$), 7.36 (s, 1H, CH$_{Ar}$), 7.72-7.82 (m, 2H, CH$_{Ar}$), 8.02 (s, 1H, CH$_{Ar}$), 10.59 (s, 1H, NH), 12.85 (s, 1H, OH). | 382 | 383 [M + H]$^+$ | A | N.D. | N.D. |

TABLE 1-continued

| N | Structure | ¹H-NMR | Molecule-Mass [g/mol] | HPLC/ MS (ESI) | human IC₅₀-Value [μM] | murine IC₅₀-Value [μM] | rate IC₅₀-Value [μM] |
|---|---|---|---|---|---|---|---|
| 33 | (biphenyl-methoxy-phenyl cyclopentene carboxylic acid amide) | δ=1.85 (m$_C$, 2H, CH$_2$), 2.71 (m$_C$, 2H, CH$_2$), 2.80 (m$_C$, 2H, CH$_2$), 3.92 (s, 3H, O—CH$_3$), 7.22 (m$_C$, 1H, CH$_{Ar}$), 7.29-7.36 (m, 2H, CH$_{Ar}$), 7.45 (m$_C$, 2H, CH$_{Ar}$), 7.67-7.71 (m, 2H, CH$_{Ar}$), 8.18 (m$_C$, 1H, CH$_{Ar}$), 10.17 (s, 1H, NH). | 337 | 338 [M + H]⁺ | A | N.D. | N.D. |
| 34 | (2'-chloro-biphenyl-methoxy-phenyl cyclopentene carboxylic acid amide) | δ=1.85 (m$_C$, 2H, CH$_2$), 2.71 (m$_C$, 2H, CH$_2$), 2.80 (m$_C$, 2H, CH$_2$), 3.85 (s, 3H, O—CH$_3$), 6.98 (m$_C$, 1H, CH$_{Ar}$), 7.10 (m$_C$, 1H, CH$_{Ar}$), 7.37-7.46 (m, 3H, CH$_{Ar}$), 7.55 (m$_C$, 1H, CH$_{Ar}$), 8.17 (m$_C$, 1H, CH$_{Ar}$), 10.19 (s, 1H, NH). | 371 | 372 [M + H]⁺ | A | N.D. | N.D. |
| 35 | (3'-trifluoromethoxy-biphenyl-methoxy-phenyl cyclopentene carboxylic acid amide) | δ=1.84 (m$_C$, 2H, CH$_2$), 2.71 (m$_C$, 2H, CH$_2$), 2.80 (m$_C$, 2H, CH$_2$), 3.93 (s, 3H, O—CH$_3$), 7.26-7.35 (m, 3H, CH$_{Ar}$), 7.57 (m$_C$, 1H, CH$_{Ar}$), 7.67 (s, 1H, CH$_{Ar}$), 7.74 (m$_C$, 1H, CH$_{Ar}$), 8.23 (m$_C$, 1H, CH$_{Ar}$), 10.33 (s, 1H, NH). | 421 | 422 [M + H]⁺ | A | N.D. | N.D. |

TABLE 1-continued
| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 36 | 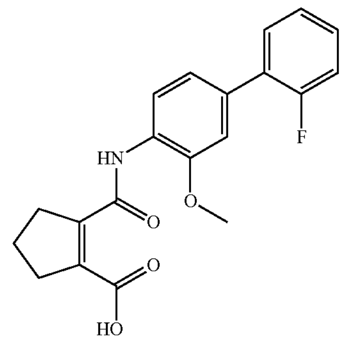 | δ=1.85 (m_C, 2H, CH₂), 2.71 (m_C, 2H, CH₂), 2.80 (m_C, 2H, CH₂), 3.88 (s, 3H, O—CH₃), 7.11 (m_C, 1H, CH_Ar), 7.19 (s, 1H, CH_Ar), 7.25-7.42 (m_C, 3H, CH_Ar), 7.56 (m_C, 1H, CH_Ar), 8.20 (m_C, 1H, CH_Ar), 10.23 (s, 1H, NH). | 355 | 356 [M + H]⁺ | A | N.D. | N.D. |
| 37 | 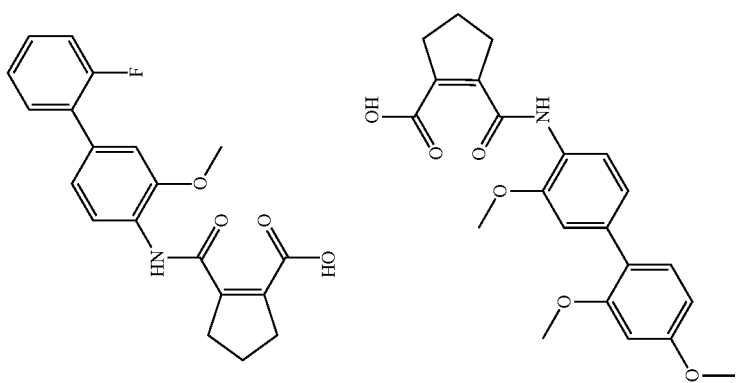 | δ=1.84 (m_C, 2H, CH₂), 2.71 (m_C, 2H, CH₂), 2.79 (m_C, 2H, CH₂), 3.76 (s, 3H, O—CH₃), 3.79 (s, 3H, O—CH₃), 3.83 (s, 3H, O—CH₃), 6.60 (m_C, 1H, CH_Ar), 6.64 (m_C, 1H, CH_Ar), 7.98 (m_C, 1H, CH_Ar), 7.08 (m_C, 1H, CH_Ar), 7.24 (m_C, 1H, CH_Ar), 8.04 (m_C, 1H, CH_Ar), 10.24 (s, 1H, NH). | 397 | 398 [M + H]⁺ | A | N.D. | N.D. |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 38 | (structure) | δ=1.34 (m$_C$, 3H, O—CH$_2$CH$_3$), 1.84 (m$_C$, 2H, CH$_2$), 2.71 (m$_C$, 2H, CH$_2$), 2.80 (m$_C$, 2H, CH$_2$), 3.92 (s, 3H, O—CH$_3$), 4.09 (m$_C$, 2H, O—CH$_2$CH3), 6.90 (m$_C$, 1H, CH$_{Ar}$), 7.18-7.24 (m$_C$, 3H, CH$_{Ar}$), 7.28 (m$_C$, 1H, CH$_{Ar}$), 7.34 (m$_C$, 1H, CH$_{Ar}$), 8.17 (m$_C$, 1H, CH$_{Ar}$), 10.20 (s, 1H, NH). | 381 | 382 [M + H]⁺ | A | N.D. | N.D. |
| 39 | (structure) | δ=1.84 (m$_C$, 2H, CH$_2$), 2.71 (m$_C$, 2H, CH$_2$), 2.80 (m$_C$, 2H, CH$_2$), 3.82 (s, 3H, O—CH$_3$), 3.92 (s, 3H, O—CH$_3$), 6.92 (m$_C$, 1H, CH$_{Ar}$), 7.20-7.26 (m, 3H, CH$_{Ar}$), 7.28 (m$_C$, 1H, CH$_{Ar}$), 7.36 (m$_C$, 1H, CH$_{Ar}$), 8.19 (m$_C$, 1H, CH$_{Ar}$), 10.24 (s, 1H, NH). | 367 | 368 [M + H]⁺ | A | N.D. | N.D. |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 40 | ![structure] | δ=1.91 (m$_C$, 2H, CH$_2$), 2.63 (m$_C$, 2H, CH$_2$), 2.74 (m$_C$, 2H, CH$_2$), 5.21 (s, 2H, O—CH$_2$), 7.22-7.89 (m, 5H, CH$_{Ar}$), 10.38 (s, 1H, NH), 12.65 (s, 1H, OH). | 545 | 546 [M + H]$^+$ | A | C | C |
| 41 | ![structure] | δ=4.22 (m$_C$, 2H, CH$_2$), 4.34 (m$_C$, 2H, CH$_2$), 7.57-7.90 (m, 8H, CH$_{Ar}$), 10.65 (s, 1H, OH). | 359 | 360 [M + H]$^+$ | A | C | C |
| 42 | ![structure] | δ=1.85 (m$_C$, 2H, CH$_2$), 2.17 (s, 2H, CH$_3$), 2.56 (m$_C$, 2H, CH$_2$), 2.65-2.70 (m, 2H, CH$_2$), 6.89-7.59 (m, 8H, CH$_{Ar}$), 10.29 (s, 1H, NH), 12.55 (s, 1H, OH). | 353 | 354 [M + H]$^+$ | A | A | A |

TABLE 1-continued

| N | Structure | ¹H-NMR | Molecule-Mass [g/mol] | HPLC/MS (ESI) | human IC₅₀-Value [µM] | murine IC₅₀-Value [µM] | rate IC₅₀-Value [µM] |
|---|---|---|---|---|---|---|---|
| 43 | (3-trifluoromethoxy-biphenyl cyclopentene carboxylic acid amide) | δ=1.94 (m_C, 2H, CH₂), 2.66 (m_C, 2H, CH₂), 2.79 (m_C, 2H, CH₂), 7.25-7.76 (m, 8H, CH_Ar), 10.36 (s, 1H, NH). | 391 | 392 [M + H]⁺ | A | N.D. | N.D. |
| 44 | (benzothiophene phenyl cyclopentene carboxylic acid amide) | δ=2.03 (m_C, 2H, CH₂), 2.77 (m_C, 2H, CH₂), 2.88 (m_C, 2H, CH₂), 7.41-8.07 (m, 9H, CH_Ar), 10.55 (s, 1H, NH), 12.83 (s, 1H, OH). | 363 | 364 [M + H]⁺ | A | N.D. | N.D. |

TABLE 1-continued

| N | Structure | ¹H-NMR | Molecule-Mass [g/mol] | HPLC/MS (ESI) | human IC₅₀-Value [µM] | murine IC₅₀-Value [µM] | rate IC₅₀-Value [µM] |
|---|---|---|---|---|---|---|---|
| 45 | (benzothiophene-phenyl-F-NH-C(O)-cyclopentene-COOH) | δ=1.74 (m_C, 2H, CH₂), 2.55 (m_C, 2H, CH₂), 2.64 (m_C, 2H, CH₂), 7.18-8.02 (m, 8H, CH_Ar), 10.55 (s, 1H, NH), 12.91 (s, 1H, OH). | 381 | 382 [M + H]⁺ | A | N.D. | N.D. |
| 46 | (ethoxy-biphenyl-F-NH-C(O)-cyclopentene-COOH) | δ=1.19 (s, 3H, O—CH₂—CH₃), 1.74 (m_C, 2H, CH₂), 2.54 (m_C, 2H, CH₂), 2.65 (m_C, 2H, CH₂), 3.95 (m_C, 2H, O—CH₂—CH₃), 6.75-6.78 (m, 1H, CH_Ar), 7.04-7.38 (m, 3H, CH_Ar), 7.43-7.48 (m, 2H, CH_Ar), 7.87-7.93 (m, 1H, CH_Ar), 10.41 (s, 1H, NH), 12.90 (s, 1H, OH). | 369 | 370 [M + H]⁺ | A | C | C |

TABLE 1-continued

| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 47 | 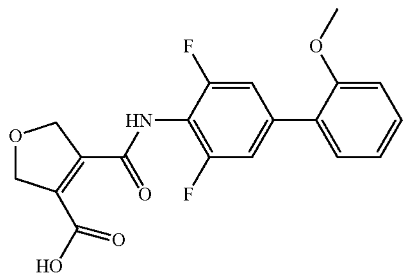 | δ=4.00 (s, 3H, O—CH₃), 5.10-5.11 (m, 4H, CH₂), 7.25-7.60 (m, 6H, CH_Ar), 10.55 (s, 1H, NH). | 375 | 376 [M + H]⁺ | A | C | A |
| 48 | 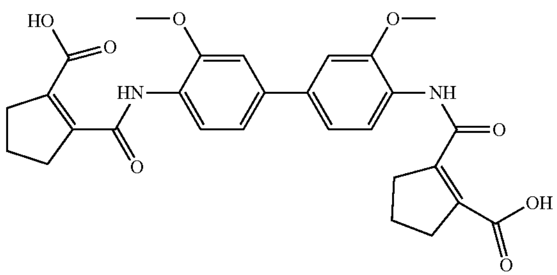 | δ=1.85 (m_C, 4H, CH₂), 2.75 (m_C, 8H, CH₂), 3.93 (s, 6H, O—CH₃), 7.25-8.19 (m, 6H, CG_Ar), 10.13 (s, 2H, NH), 13.18 (s, 2H, OH). | 521 | 521 [M + H]⁺ | C | N.D. | N.D. |
| 49 | 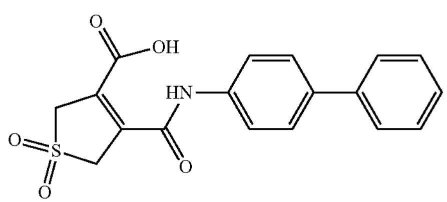 | δ=4.24-4.40 (m, 4H, CH₂), 7.30-7.74 (m, 9H, CH_Ar), 10.72 (s, 1H, NH). | 357 | 358 [M + H]⁺ | C | N.D. | N.D. |
| 50 | 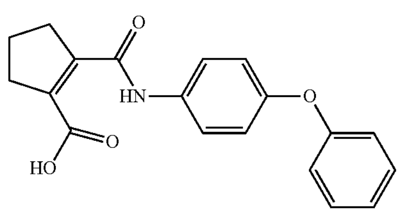 | δ=1.90 (m_C, 2H, CH₂), 2.64 (m_C, 2H, CH₂), 2.76 (m_C, 2H, CH₂), 6.94-7.64 (m, 9H, CH_Ar), 10.25 (s, 1H, NH), 12.73 (s, 1H, OH). | 323 | 324 [M + H]⁺ | A | A | A |

TABLE 1-continued

| N | Structure | $^1$H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 51 | 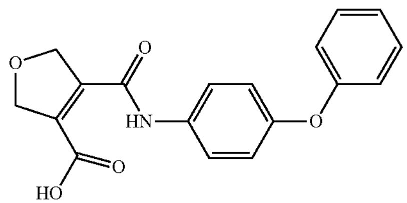 | δ=4.84 (m$_C$, 2H, CH$_2$), 4.94 (m$_C$, 2H, CH$_2$), 6.61-7.63 (m, 9H, CH$_{Ar}$), 11.24 (s, 1H, NH). | 325 | 326 [M + H]$^+$ | C | N.D. | N.D. |
| 52 | 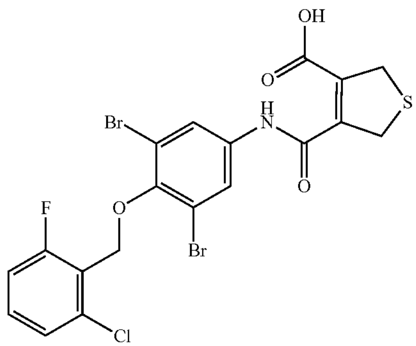 | δ=4.08 (m$_C$, 4H, CH$_2$), 5.21 (m$_C$, 2H, CH$_2$), 6.61-7.63 (m, 9H, CH$_{Ar}$), 11.24 (s, 1H, NH). | 563 | 564 [M + H]$^+$ | A | B | A |
| 53 | 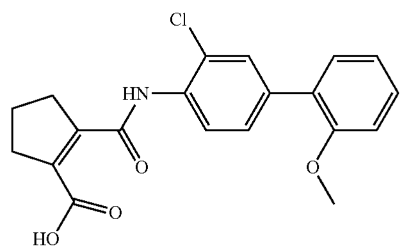 | δ(CDCl3)=2.03 (m$_C$, 2H, CH$_2$), 3.01-3.09 (m, 4H, CH$_2$), 3.81 (s, 3H, O—CH$_3$), 6.96-7.05 (m, 2H, CH$_{Ar}$), 7.26-7.37 (m, 2H, CH$_{Ar}$), 7.50 (m$_C$, 1H, CH$_{Ar}$), 7.63 (s, 1H, CH$_{Ar}$), 8.36-8.39 (m, 2H, NH and CH$_{Ar}$). | 371 | 372 [M + H]$^+$ | A | B | B |

TABLE 1-continued

| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 54 | (2-methoxybiphenyl with Cl, cyclopentene carboxylic acid amide) | δ(CD3OD)=2.00 (m$_C$, 2H, CH$_2$), 2.81 (m$_C$, 2H, CH$_2$), 2.9 (m$_C$, 2H, CH$_2$), 3.76 (s, 3H, O—CH$_3$), 6.97-7.07 (m, 2H, CH$_{Ar}$), 7.14 (m$_C$, 1H, CH$_{Ar}$), 7.22 (m$_C$, 1H, CH$_{Ar}$), 7.37 (m$_C$, 1H, CH$_{Ar}$), 7.50 (m$_C$, 1H, CH$_{Ar}$), 7.85 (m$_C$, 1H, CH$_{Ar}$). | 371 | 372 [M + H]⁺ | A | B | A |
| 55 | (2-methoxybiphenyl with CF$_3$, cyclopentene carboxylic acid amide) | δ(CD3OD)=1.99 (m$_C$, 2H, CH$_2$), 2.81-2.93 (m, 4H, CH$_2$), 3.81 (s, 3H, O—CH$_3$), 7.01-7.11 (m, 2H, CH$_{Ar}$), 7.31-7.40 (m, 2H, CH$_{Ar}$), 7.67-7.77 (m, 2H, CH$_{Ar}$), 7.82 (m$_C$, 1H, CH$_{Ar}$). | 405 | 406 [M + H]⁺ | C | N.D. | N.D. |
| 56 | (tetrafluoro-2-methoxybiphenyl, cyclopentene carboxylic acid amide) | δ(DMSO-d6)=1.93 (m$_C$, 2H, CH$_2$), 2.67 (m$_C$, 2H, CH$_2$), 2.79 (m$_C$, 2H, CH$_2$), 3.79 (s, 3H, O—CH$_3$), 7.09 (m$_C$, 1H, CH$_{Ar}$), 7.20 (m$_C$, 1H, CH$_{Ar}$), 7.37 (m$_C$, 1H, CH$_{Ar}$), 7.51 (m$_C$, 1H, CH$_{Ar}$). | 409 | 410 [M + H]⁺ | A | A | A |

TABLE 1-continued

| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 57 | 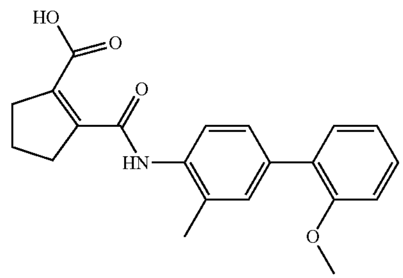 | δ(CD3OD)=1.97 (m_C, 2H, CH₂), 2.33 (s, 3H, CH₃), 2.84 (m_C, 2H, CH₂), 2.94 (m_C, 2H, CH₂), 3.78 (s, 3H, O—CH₃), 6.96-7.06 (m, 2H, CH_Ar), 7.25-7.35 (m, 4H, CH_Ar), 7.50 (s, 1H, CH_Ar). | 351 | 352 [M + H]⁺ | A | B | B |
| 58 | 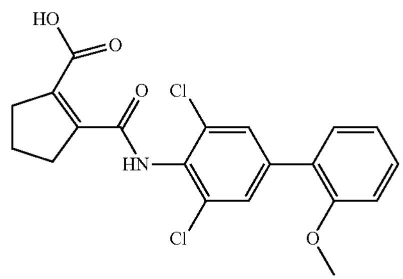 | δ(CD3OD)=1.93 (m_C, 2H, CH₂), 2.87-2.95 (m, 4H, CH₂), 3.83 (s, 3H, O—CH₃), 7.01-7.10 (m, 2H, CH_Ar), 7.29-7.37 (m, 2H, CH_Ar), 7.56 (s, 2H, CH_Ar). | 405 | 406 [M + H]⁺ | A | B | B |
| 59 | 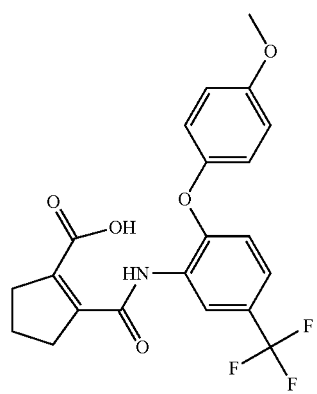 | δ(CD3OD) =1.91 (m_C, 2H, CH₂), 2.87-2.90 (m, 4H, CH₂), 3.78 (s, 3H, O—CH₃), 6.85 (m_C, 1H, CH_Ar), 6.94 (m_C, 2H, CH_Ar), 7.03 (m_C, 2H, CH_Ar), 7.32 (m_C, 1H, CH_Ar), 8.60 (m_C, 1H, CH_Ar). | 421 | 422 [M + H]⁺ | C | N.D. | N.D. |

TABLE 1-continued

| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 60 | 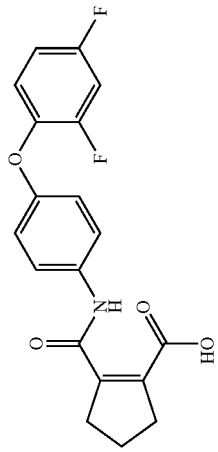 | δ=1.70 (m_C, 2H, CH₂), 2.45 (m_C, 2H, CH₂), 2.56 (m_C, 2H, CH₂), 6.75 (m_C, 2H, CH_Ar), 6.86-7.05 (m, 2H, CH_Ar), 7.22-7.29 (m, 1H, CH_Ar), 7.40 (m_C, 2H, CH_Ar), 10.07 (s, 1H, NH). | 359 | 360 [M + H]⁺ | B | N.D. | N.D. |
| 61 | 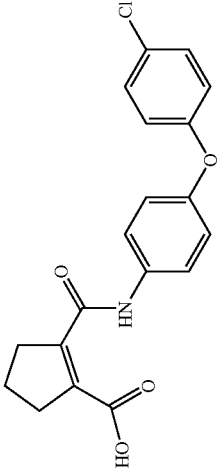 | δ(DMSO-d6)=1.87 (m_C, CH₂), 2.62 (m_C, 2H, CH₂), 2.73 (m_C, 2H, CH₂), 6.95 (m_C, 2H, CH_Ar), 6.98 (m_C, 2H, CH_Ar), 7.36 (m_C, 2H, CH_Ar), 7.60 (m_C, 2H, CH_Ar), 10.32 (s, 1H, NH). | 357 | 358 [M + H]⁺ | C | N.D. | N.D. |
| 62 | 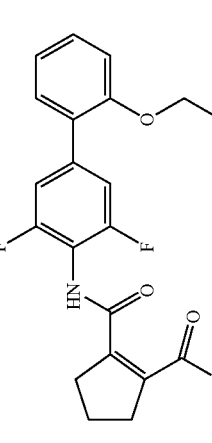 | δ(CD3OD)=1.35 (m_C, 3H, OCH₂CH₃), 2.00 (m_C, 2H, CH₂), 2.84 (m_C, 2H, CH₂), 2.94 (m_C, 2H, CH₂), 4.07 (m_C, 2H, OCH₂CH₃), 6.98-7.08 (m, 2H, CH_Ar), 7.23 (m_C, 2H, CH_Ar), 7.30-7.37 (m, 2H, CH_Ar). | 387 | 388 [M + H]⁺ | A | B | A |
| 63 | 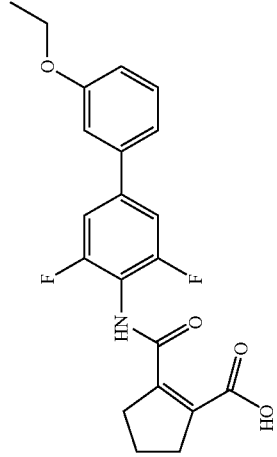 | δ(CD3OD)=1.40 (m_C, 3H, OCH₂CH₃), 1.99 (m_C, 2H, CH₂), 2.84 (m_C, 2H, CH₂), 2.93 (t, J=7.5 Hz, 2H, CH₂), 4.09 (m_C, 2H, OCH₂CH₃), 6.94 (m_C, 1H, CH_Ar), 7.13-7.20 (m, 2H, CH_Ar), 7.30-7.38 (m, 3H, CH_Ar). | 387 | 388 [M + H]⁺ | A | B | A |

TABLE 1-continued

| N | Structure | ¹H-NMR | Molecule-Mass [g/mol] | HPLC/MS (ESI) | human IC₅₀-Value [μM] | murine IC₅₀-Value [μM] | rate IC₅₀-Value [μM] |
|---|---|---|---|---|---|---|---|
| 64 | (3-trifluoromethoxyphenyl)-2,6-difluoroanilide of cyclopentene-1,2-dicarboxylic acid | δ(CD3OD)=1.99 (m$_C$, 2H, CH$_2$), 2.85 (m$_C$, 2H, CH$_2$), 2.91 (m$_C$, 2H, CH2), 7.31-7.39 (m, 3H, CH$_{Ar}$), 7.54-7.59 (m, 2H, CHAr), 7.66 (m$_C$, 2H, CH$_{Ar}$). | 427 | 428 [M + H]⁺ | A | C | N.D. |
| 65 | (2-chlorobiphenyl)-2,6-difluoroanilide of cyclopentene-1,2-dicarboxylic acid | δ(CD3OD)=2.00 (m$_C$, 2H, CH$_2$), 2.84 (m$_C$, 2H, CH$_2$), 2.94 (m$_C$ 2H, CH$_2$), 7.12 (s, 1H, CH$_{Ar}$), 7.14 (s, 1H, CH$_{Ar}$), 7.37-7.42 (m, 3H, CH$_{Ar}$), 7.49-7.53 (m, 1H, CH$_{Ar}$). | 377 | 378 [M + H]⁺ | A | A | N.D. |
| 66 | (2-fluorobiphenyl)-2,6-difluoroanilide of cyclopentene-1,2-dicarboxylic acid | δ(CD3OD)=2.00 (m$_C$, 2H, CH$_2$), 2.84 (m$_C$, 2H, CH$_2$), 2.94 (t, J=7.8 Hz, 2H, CH$_2$), 7.18-7.30 (m, 4H, CH$_{Ar}$), 7.38-7.46 (m, 1H, CH$_{Ar}$), 7.46-7.55 (m, 1H, CH$_{Ar}$). | 361 | 362 [M + H]⁺ | A | B | N.D. |

TABLE 1-continued

| N | Structure | $^1$H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 67 | 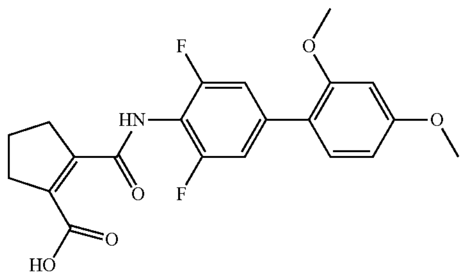 | δ(CD3OD)=1.94(m$_C$, 2H, CH$_2$), 2.84-2.92 (m, 4H, CH$_2$), 3.82 (s, 3H, O—CH$_3$), 3.83 (s, 3H, O—CH$_3$), 6.58-6.64 (m, 2H, CH$_{Ar}$), 7.14 (s, 1H, CH$_{Ar}$), 7.17 (s, 1H, CH$_{Ar}$), 7.26 (m$_C$, 1H, CH$_{Ar}$). | 403 | 404 [M + H]$^+$ | A | C | N.D. |
| 68 | 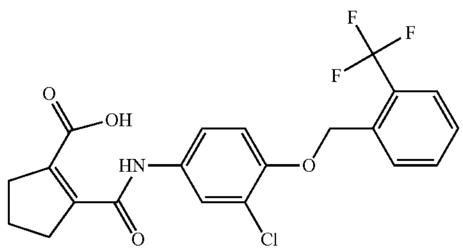 | δ=1.90 (m$_C$, 2H, CH$_2$), 2.63 (m$_C$, 2H, CH$_2$), 2.74 (m$_C$, 2H, CH$_2$), 5.27 (s, 2H, O—CH$_2$), 7.19-7.82 (m, 7H, CH$_{Ar}$), 10.23 (s, 1H, NH), 12.69 (s, 1H, OH). | 439 | 440 [M + H]$^+$ | A | C | C |
| 69 | 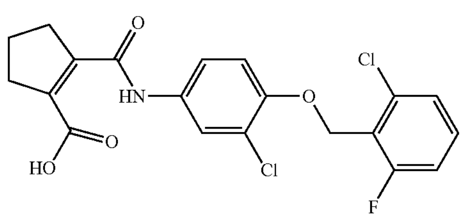 | δ=1.89 (m$_C$, 2H, CH$_2$), 2.62 (m$_C$, 2H, CH$_2$), 2.74 (m$_C$, 2H, CH$_2$), 5.18 (m$_C$, 2H, O—CH$_2$), 7.27-7.77 (m, 6H, CH$_{Ar}$), 10.21 (s, 1H, NH), 12.69 (s, 1H, OH). | 423 | 424 [M + H]$^+$ | A | A | N.D. |
| 70 | 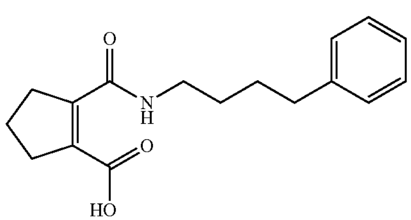 | δ=1.44-1.62 (m, 4H, CH$_2$), 1.79 (m$_C$, 2H, CH$_2$), 2.55-2.75 (m, 6H, CH$_2$), 3.15-3.22 (m, 2H, NH—CH$_2$), 7.13-7.29 (m, 5H, CH$_{Ar}$), 8.53 (m$_C$, 1H, NH), 14.84 (s, 1H, OH). | 287 | 288 [M + H]$^+$ | C | N.D. | N.D. |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 71 | 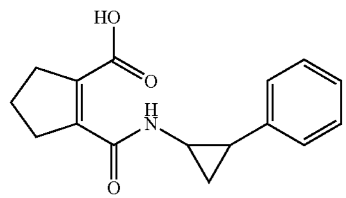 | δ=1.26 (m$_C$, 2H, CH$_2$), 1.81 (m$_C$, 2H, CH$_2$), 2.05 (m$_C$, 1H, CH), 2.63 (m$_C$, 2H, CH$_2$), 2.71 (m$_C$, 2H, CH$_2$), 2.90 (m$_C$, 1H, CH), 7.10-7.28 (m, 5H, CH$_{Ar}$), 8.61-8.62 (m, 1H, NH), 14.12 (s, 1H, OH). | 271 | 272 [M+H]$^+$ | C | N.D. | N.D. |
| 72 | 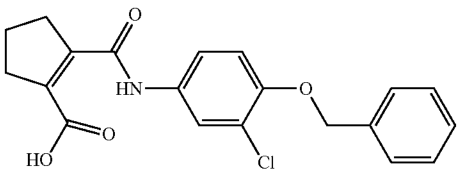 | δ=1.73 (m$_C$, 2H, CH$_2$), 2.46 (m$_C$, 2H, CH$_2$), 2.57 (m$_C$, 2H, CH$_2$), 4.99 (m$_C$, 2H, O—CH$_2$), 7.00-7.62 (m, 8H, CH$_{Ar}$), 10.02 (s, 1H, NH), 12.70 (s, 1H, OH). | 371 | 372 [M+H]$^+$ | A | B | N.D. |
| 73 | 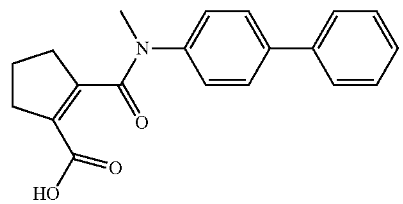 | δ=1.47 (m$_C$, 2H, CH$_2$), 2.13-2.45 (m, 2H, CH$_2$), 2.34-2.36 (m, 2H, CH$_2$), 3.10 (s, 3H, N—CH$_3$), 7.20-7.55 (m, 9H, CH$_{Ar}$), 12.32 (s, 1H, OH). | 321 | 322 [M+H]$^+$ | C | N.D. | N.D. |
| 74 | 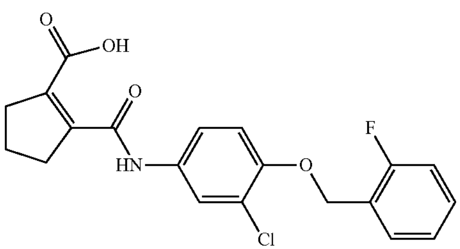 | δ=1.82 (m$_C$, 2H, CH$_2$), 2.55 (m$_C$, 2H, CH$_2$), 2.67 (m$_C$, 2H, CH$_2$), 5.11 (m$_C$, 2H, O—CH$_2$), 7.14-7.72 (m, 7H, CH$_{Ar}$), 10.18 (s, 1H, NH), 12.53 (s, 1H, OH). | 389 | 390 [M+H]$^+$ | A | A | N.D. |

TABLE 1-continued

| N | Structure | ¹H-NMR | Molecule-Mass [g/mol] | HPLC/MS (ESI) | human IC₅₀-Value [µM] | murine IC₅₀-Value [µM] | rate IC₅₀-Value [µM] |
|---|---|---|---|---|---|---|---|
| 75 | (structure) | δ=1.98 (m$_C$, 2H, CH$_2$), 2.62-2.83 (m, 4H, CH$_2$), 6.79-7.85 (m, 9H, CH$_{Ar}$), 9.53 (s, 1H, OH). | 308 | 309 [M + H]⁺ | C | N.D. | N.D. |
| 76 | (structure) | δ(CDCl3)=2.01 (m$_C$, 2H, CH$_2$), 2.99-3.04 (m, 4H, CH$_2$), 3.81 (s, 3H, O—CH$_3$), 6.96-7.04 (m, 2H, CH$_{Ar}$), 7.27-7.41 (m, 4H, CH$_{Ar}$), 8.19 (s, 1H, NH), 8.28 (m$_C$ 1H, CH$_{Ar}$). | 355 | 356 [M + H]⁺ | A | B | A | abbreviations: N.D. = not determined, m$_C$ = multiplet center
inhibition activity is defined: A: 0-800 nM B: 800-1500 nM C: >1500 nM 3. Proliferation Assay of Human T-Cells Buffy coats of healthy donors were obtained from the local Red Cross; from these human mononuclear cells (MNC) were isolated using Accuspin™ System-Histopaque-1077 (Sigma) according to the protocol recommended by the manufacturer. Cells were seeded at densities of $5\times10^4$ or $1\times10^5$ cells per well in 96 well flat bottom plates in RPMI 1640 supplemented with 10% fetal calf serum, 2 mM L-glutamine and penicillin/streptomycin. Cells were activated with 1 μg/ml phytohaemagglutinin (PHA, Sigma) or 20 nM PMA (phorbol-12-myristate-13-acetate)/10 μM ionomycin (Calbiochem) and incubated with the test compounds in a final volume of 100 μl for 48 hours. Proliferation was measured using the CellTiter 96® Aqueous One Solution Cell Proliferation Assay (Promega) according to the lymphocyte assay protocol supplied by the manufacturer.

2-(Biphenyl-4-ylcarbamoyl)-cyclopent-1-enecarboxylic acid (100 μM) caused a reduction of human lymphocyte cell proliferation of 40% indicating that the compound has an inhibitory effect on DHODH in vivo (see FIG. 1).

The invention claimed is:

1. A compound of Formula (I) and any salt thereof,

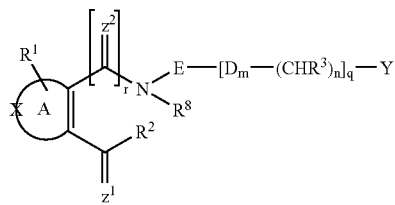

Formula (I)

wherein
- A is a non-aromatic ring system containing five carbon atoms, wherein the ring system comprises at least one double bond and wherein one or more of the carbon atoms in the ring can be replaced by a group X, wherein X is selected from the group consisting of S, O, N, $NR^4$, SO or $SO_2$, and wherein one or more of the carbon atoms of the ring can carry a substituent $R^1$;
- D is O, S, $SO_2$, $NR^4$, or $CH_2$;
- $Z^1$ and $Z^2$ are independent from each other O, S, or $NR^5$;
- $R^1$ is independently H, halogen, haloalkyl, haloalkyloxy or alkyl;
- $R^2$ is H, $OR^6$, or $NHR^7$;
- $R^3$ is H, alkyl, cycloalkyl, aryl, arylalkyl, alkoxy, O-aryl; O-cycloalkyl, halogen, aminoalkyl, alkylamino, hydroxylamino, hydroxylalkyl, haloalkyl, haloalkyloxy, heteroaryl, alkylthio, S-aryl, or S-cycloalkyl;
- $R^4$ is H, alkyl, cycloalkyl, aryl, or heteroaryl;
- $R^5$ is H, OH, alkoxy, O-aryl, alkyl, or aryl;
- $R^6$ is H, alkyl, cycloalkyl, aryl, heteroaryl, arylalkyl, alkylaryl, alkoxyalkyl, acylmethyl, (acyloxy)alkyl, non-symmetrical (acyloxy)alkyldiester, or dialkylphosphate;
- $R^7$ is H, alkyl, aryl, alkoxy, O-aryl, cycloalkyl, or O-cycloalkyl;
- $R^8$ is hydrogen or alkyl;
- E is an alkyl or cycloalkyl group or a monocyclic or polycyclic substituted or unsubstituted ring system which may contain one or more groups X and which contains at least one aromatic ring;
- Y is hydrogen, halogen, haloalkyl, haloalkyloxy, alkyl, cycloalkyl, a monocyclic or polycyclic substituted or unsubstituted ring system which may contain one or more groups X and which contains at least one aromatic ring or

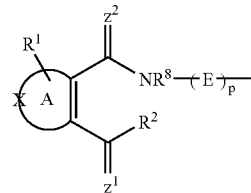

- m is 0 or 1;
- n is 0 or 1;
- p is 0 or 1;
- r is 0 or 1; and
- q is 0 to 10;

and wherein
- alkyl denotes a saturated or unsaturated alkyl group, which is optionally substituted by one or more substituents R';
- R' is independently H, $-NO_2$, $-CO_2R''$, $-CONHR''$, $-CR''O$, $-SO_2NR''$, $-NR''-CO$-haloalkyl, $-NR'-SO_2$-haloalkyl, $-NR''-SO_2$-alkyl, $-SO_2$-alkyl, $-NR''-CO$-alkyl, $-CN$, alkyl, cycloalkyl, aminoalkyl, alkylamino, alkoxy, $-OH$, $-SH$, alkylthio, hydroxyalkyl, hydroxyalkylamino, halogen, haloalkyl, haloalkyloxy, aryl, arylalkyl or heteroaryl;
- R'' is independently hydrogen, haloalkyl, hydroxyalkyl, alkyl, cycloalkyl, aryl, heteroaryl or aminoalkyl;
- an cycloalkyl group denotes a non-aromatic ring system containing 3 to 8 carbon atoms, wherein one or more of the carbon atoms in the ring can be replaced by a group X, X being as defined above;
- an alkoxy group denotes an O-alkyl group, the alkyl group being as defined above;
- an alkylthio group denotes a S-alkyl group, the alkyl group being as defined above;
- an hydroxyalkyl group denotes a S-alkyl group, the alkyl group being as defined above;
- an haloalkyl group denotes an alkyl group which is substituted by one to five preferably three halogen atoms, the alkyl group being as defined above;
- an haloalkyloxy group denotes an alkoxy group which is substituted by one to five preferably three halogen atoms, the alkoxy group being as defined above;
- a hydroxyalkylamino group denotes an $(HO-alkyl)_2$—N-group or HO-alkyl-NH-group, the alkyl group being as defined above;
- an alkylamino group denotes an HN-alkyl or N-dialkyl group, the alkyl group being as defined above;
- an amino alkyl group denotes an $H_2N$-alkyl, monoalkylaminoalkyl, or dialkylaminoalkyl group, the alkyl group being as defined above;
- a halogen group is chlorine, bromine, fluorine or iodine;
- an aryl group denotes an aromatic group having 5 to 15 carbon atoms, which is optionally substituted by one or more substituents R', where R' is as defined above;
- an arylakyl group denotes an alky group which is substituted by one to three aryl groups, the alkyl and aryl group being as defined above;
- a heteroaryl group denotes a 5- or 6-membered heteroaromatic group which contains at least one heteroatom selected from O, N, S, which may be fused to another ring and which is optionally substituted by one or more substituents R', where R' is as defined above.

2. The compound of claim 1, wherein $Z^1$ and $Z^2$ are both O and r=1.

3. The compound of claim 1, wherein r=1, and E is phenyl, 1-napthyl, 2-naphthyl, 2-naphthyl, 1-anthracenyl, 2-anthracenyl, 9H-thioxanthene-10,10-dioxide, or cycloalkyl.

4. The compound of claim 1, wherein $Z^1$ and $Z^2$ are both O and r=1 and E is phenyl, 1-napthyl, 2-naphthyl, 2-naphthyl, 1-anthracenyl, 2-anthracenyl, 9H-thioxanthene-10,10-dioxide, or cycloalkyl.

5. The compound of claim 1, wherein E is phenyl, 1-napthyl, 2-naphthyl, 2-naphthyl, 1-anthracenyl, 2-anthracenyl, 9H-thioxanthene-10,10-dioxide, or cycloalkyl and r=1, and $R^2$ is OH or $OR^6$.

6. The compound of claim 1, wherein $Z^1$ and $Z^2$ are both O, and r=1, and E is phenyl, 1-napthyl, 2-naphthyl, 2-naphthyl, 1-anthracenyl, 2-anthracenyl, 9H-thioxanthene-10,10-dioxide, or cycloalkyl and $R^2$ is OH or $OR^6$.

7. A pharmaceutical composition comprising a compound as defined in claim 1 in free form or in the form of a pharmaceutically acceptable salt and physiologically functional derivative, together with at least one pharmaceutically acceptable diluent or carrier.

8. A method of making the pharmaceutical composition of claim 7, comprising combining the compound with the pharmaceutically acceptable diluent or carrier.

9. A method for the in vitro inhibition of dihydroorotate dehydrogenase (DHODH) comprising
providing a sample containing dihydroorotate dehydrogenase (DHODH); and
adding to the sample a compound as defined in claim 1.

10. A method of inhibiting dihydroorotate dehydrogenase (DHODH), for treating rheumatism, diseases that are caused by protozoal infestations in humans and animals, Pneumocystis carinii, fibrosis, uveitis, rhinitis, asthma, athropathy, sepsis, septic shock, endotoxic shock, Gram-negative sepsis, toxic shock syndrome, acute respiratory distress syndrome, stroke, reperfusion injury, CNS injury, allergy, graft versus host reactions, host versus graft reactions, pyresis, restenosis, chronic pulmonary inflammatory disease, silicosis, pulmonary sarcosis, bone resorption disease, rheumatoid spondylitis, osteoarthritis, gouty arthritis, insulin dependent diabetes mellitus, non-insulin dependent diabetes, ulcerative colitis, Morbus Crohn, inflammatory bowel disease, chronic inflammations, chronic diarrhea, psoriasis and progressive retinal atrophy in a subject, comprising administering an effective amount of a compound to the subject, wherein the compound is of Formula (I) and any salt thereof, Formula I

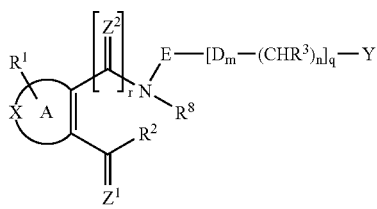

wherein

A is a non-aromatic ring system containing five carbon atoms, wherein the ring system comprises at least one double bond and wherein one or more of the carbon atoms in the ring can be replaced by a group X, wherein X is selected from the group consisting of S, O, N, $NR^4$, SO or $SO_2$, and wherein one or more of the carbon atoms of the ring can carry a substituent $R^1$;

D is O, S, $SO_2$, $NR^4$, or $CH_2$;

$Z^1$ and $Z^2$ are independent from each other O, S, or $NR^5$;

$R^1$ is independently H, halogen, haloalkyl, haloalkyloxy or alkyl;

$R^2$ is H, $OR^6$, or $NHR^7$;

$R^3$ is H, alkyl, cycloalkyl, aryl, arylalkyl, alkoxy, O-aryl; O-cycloalkyl, halogen, aminoalkyl, alkylamino, hydroxylamino, hydroxylalkyl, haloalkyl, haloalkyloxy, heteroaryl, alkylthio, S-aryl, or S-cycloalkyl;

$R^4$ is H, alkyl, cycloalkyl, aryl, or heteroaryl;

$R^5$ is H, OH, alkoxy, O-aryl, alkyl, or aryl;

$R^6$ is H, alkyl, cycloalkyl, aryl, heteroaryl, arylalkyl, alkylaryl, alkoxyalkyl, acylmethyl, (acyloxy)alkyl, non-symmetrical (acyloxy)alkyldiester, or dialkylphosphate;

$R^7$ is H, alkyl, aryl, alkoxy, O-aryl, cycloalkyl, or O-cycloalkyl;

$R^8$ is hydrogen or alkyl;

E is an alkyl or cycloalkyl group or a monocyclic or polycyclic substituted or unsubstituted ring system which may contain one or more groups X and which contains at least one aromatic ring;

Y is hydrogen, halogen, haloalkyl, haloalkyloxy, alkyl, cycloalkyl, a monocyclic or polycyclic substituted or unsubstituted ring system which may contain one or more groups X and which contains at least one aromatic ring or

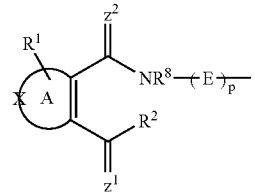

m is 0 or 1;
n is 0 or 1;
p is 0 or 1;
r is 0 or 1; and
q is 0 to 10;
and wherein alkyl denotes a saturated or unsaturated alkyl group, which is optionally substituted by one or more substituents R';

R' is independently H, $-NO_2$, $-CO_2R''$, $-CONHR''$, $-CR''O$, $-SO_2NR''$, $-NR''-CO$-haloalkyl, $-NR'-SO_2$-haloalkyl, $-NR''-SO_2$-alkyl, $-SO_2$-alkyl, $-NR''-CO$-alkyl, $-CN$, alkyl, cycloalkyl, aminoalkyl, alkylamino, alkoxy, $-OH$, $-SH$, alkylthio, hydroxyalkyl, hydroxyalkylamino, halogen, haloalkyl, haloalkyloxy, aryl, arylalkyl or heteroaryl;

R'' is independently hydrogen, haloalkyl, hydroxyalkyl, alkyl, cycloalkyl, aryl, heteroaryl or aminoalkyl;

an cycloalkyl group denotes a non-aromatic ring system containing 3 to 8 carbon atoms, wherein one or more of the carbon atoms in the ring can be replaced by a group X, X being as defined above;

an alkoxy group denotes an O-alkyl group, the alkyl group being as defined above;

an alkylthio group denotes a S-alkyl group, the alkyl group being as defined above;

an hydroxyalkyl group denotes a S-alkyl group, the alkyl group being as defined above;

an haloalkyl group denotes an alkyl group which is substituted by one to five preferably three halogen atoms, the alkyl group being as defined above;

an haloalkyloxy group denotes an alkoxy group which is substituted by one to five preferably three halogen atoms, the alkoxy group being as defined above;

a hydroxyalkylamino group denotes an (HO-alkyl)$_2$—N-group or HO-alkyl-NH-group, the alkyl group being as defined above;

an alkylamino group denotes an HN-alkyl or N-dialkyl group, the alkyl group being as defined above;

an amino alkyl group denotes an H$_2$N-alkyl, monoalkylaminoalkyl, or dialkylaminoalkyl group, the alkyl group being as defined above;

a halogen group is chlorine, bromine, fluorine or iodine;

an aryl group denotes an aromatic group having 5 to 15 carbon atoms, which is optionally substituted by one or more substituents R', where R' is as defined above;

an arylakyl group denotes an alky group which is substituted by one to three aryl groups, the alkyl and aryl group being as defined above;

a heteroaryl group denotes a 5- or 6-membered heteroaromatic group which contains at least one heteroatom selected from O, N, S, which may be fused to another ring and which is optionally substituted by one or more substituents R', where R' is as defined above.

11. The method of claim 10, wherein the disease is selected from the group consisting of rheumatism, diseases that are caused by protozoal infestations in humans and animals, Pneumocystis carinii, fibrosis, uveitis, rhinitis, asthma, and athropathy.

12. A method of treating at least one condition selected from the group consisting of sepsis, septic shock, endotoxic shock, Gram-negative sepsis, toxic shock syndrome, acute respiratory distress syndrome, stroke, reperfusion injury, CNS injury, allergy, graft versus host reactions, host versus graft reactions, pyresis, restenosis, chronic pulmonary inflammatory disease, silicosis, pulmonary sarcosis, bone resorption disease, rheumatoid spondylitis, osteoarthritis, gouty arthritis, insulin dependent diabetes mellitus and non-insulin dependent diabetes, ulcerative colitis, Morbus Crohn, inflammatory bowel disease, chronic diarrhea, psoriasis and progressive retinal atrophy, compromising administering an effective amount of a compound to a subject, wherein the compound is of Formula (I) and any salt thereof,

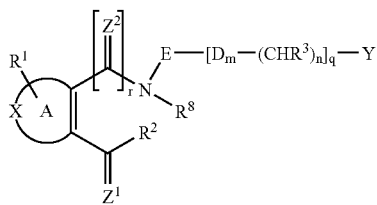

Formula I wherein

A is a non-aromatic ring system containing five carbon atoms, wherein the ring system comprises at least one double bond and wherein one or more of the carbon atoms in the ring can be replaced by a group X, wherein X is selected from the group consisting of S, O, N, NR$^4$, SO or SO$_2$, and wherein one or more of the carbon atoms of the ring can carry a substituent R$^1$;

D is O, S, SO$_2$, NR$^4$, or CH$_2$;

Z$^1$ and Z$^2$ are independent from each other O, S, or NR$^5$;

R$^1$ is independently H, halogen, haloalkyl, haloalkyloxy or alkyl;

R$^2$ is H, OR$^6$, or NHR$^7$;

R$^3$ is H, alkyl, cycloalkyl, aryl, arylalkyl, alkoxy, O-aryl; O-cycloalkyl, halogen, aminoalkyl, alkylamino, hydroxylamino, hydroxylalkyl, haloalkyl, haloalkyloxy, heteroaryl, alkylthio, S-aryl, or S-cycloalkyl;

R$^4$ is H, alkyl, cycloalkyl, aryl, or heteroaryl;

R$^5$ is H, OH, alkoxy, O-aryl, alkyl, or aryl;

R$^6$ is H, alkyl, cycloalkyl, aryl, heteroaryl, arylalkyl, alkylaryl, alkoxyalkyl, acylmethyl, (acyloxy)alkyl, non-symmetrical (acyloxy)alkyldiester, or dialkylphosphate;

R$^7$ is H, alkyl, aryl, alkoxy, O-aryl, cycloalkyl, or O-cycloalkyl;

R$^8$ is hydrogen or alkyl;

E is an alkyl or cycloalkyl group or a monocyclic or polycyclic substituted or unsubstituted ring system which may contain one or more groups X and which contains at least one aromatic ring;

Y is hydrogen, halogen, haloalkyl, haloalkyloxy, alkyl, cycloalkyl, a monocyclic or polycyclic substituted or unsubstituted ring system which may contain one or more groups X and which contains at least one aromatic ring or

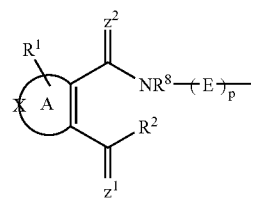

m is 0 or 1;
n is 0 or 1;
p is 0 or 1;
r is 0 or 1; and
q is 0 to 10;

and wherein alkyl denotes a saturated or unsaturated alkyl group, which is optionally substituted by one or more substituents R';

R' is independently H, —NO$_2$, —CO$_2$R", —CONHR", —CR"O, —SO$_2$NR", —NR"—CO-haloalkyl, —NR'—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R" is independently hydrogen, haloalkyl, hydroxyalkyl, alkyl, cycloalkyl, aryl, heteroaryl or aminoalkyl;

an cycloalkyl group denotes a non-aromatic ring system containing 3 to 8 carbon atoms, wherein one or more of the carbon atoms in the ring can be replaced by a group X, X being as defined above;

an alkoxy group denotes an O-alkyl group, the alkyl group being as defined above;

an alkylthio group denotes a S-alkyl group, the alkyl group being as defined above;

an hydroxyalkyl group denotes a S-alkyl group, the alkyl group being as defined above;

an haloalkyl group denotes an alkyl group which is substituted by one to five preferably three halogen atoms, the alkyl group being as defined above;

an haloalkyloxy group denotes an alkoxy group which is substituted by one to five preferably three halogen atoms, the alkoxy group being as defined above;

a hydroxyalkylamino group denotes an (HO-alkyl)$_2$—N-group or HO-alkyl-NH-group, the alkyl group being as defined above;

an alkylamino group denotes an HN-alkyl or N-dialkyl group, the alkyl group being as defined above;

an aminoalkyl group denotes an H$_2$N-alkyl, monoalkylaminoalkyl, or dialkylaminoalkyl group, the alkyl group being as defined above;

a halogen group is chlorine, bromine, fluorine or iodine;

an aryl group denotes an aromatic group having 5 to 15 carbon atoms, which is optionally substituted by one or more substituents R', where R' is as defined above;

an arylakyl group denotes an alky group which is substituted by one to three aryl groups, the alkyl and aryl group being as defined above;

a heteroaryl group denotes a 5- or 6-membered heteroaromatic group which contains at least one heteroatom selected from O, N, S, which may be fused to another ring and which is optionally substituted by one or more substituents R', where R' is as defined above.

* * * * *